US006388175B1

(12) United States Patent
Birch et al.

(10) Patent No.: US 6,388,175 B1
(45) Date of Patent: May 14, 2002

(54) CONTROL OF LEAF SCALD DISEASE

(75) Inventors: Robert Birch, Jindalee; Lianhui Zhang, North Balwyn, both of (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 09/029,785

(22) PCT Filed: Sep. 6, 1996

(86) PCT No.: PCT/AU96/00554

§ 371 Date: Mar. 9, 1998

§ 102(e) Date: Mar. 9, 1998

(87) PCT Pub. No.: WO97/09417

PCT Pub. Date: Mar. 13, 1997

(30) Foreign Application Priority Data

Sep. 7, 1995 (AU) ................................................ PN5278

(51) Int. Cl.[7] .......................... C12N 5/04; C12N 15/31; C12N 15/82; C12N 15/52; A01H 5/00
(52) U.S. Cl. ................... 800/301; 435/69.1; 435/320.1; 435/418; 435/419; 435/470; 536/23.6; 536/23.7; 800/279; 800/288; 800/293; 800/298; 800/320
(58) Field of Search ............................. 435/69.1, 320.1, 435/410, 418, 419, 468, 470; 536/23.6, 23.7; 800/278, 279, 295, 298, 301, 293, 288, 320

(56) References Cited

PUBLICATIONS

Zhang et al, Proc. Natl. Acad Sci., USA, vol. 94, pp. 9984–9989, 1997.*
Gambley et al, Plant Cell Rep., vol. 12, pp. 343–346, 1993.*
Chen et al, J. Exper. Bot., vol. 39, pp. 251–261, 1988.*
Walker et al., "Cloning and characterization of an albicidin resistance gene from *Klebsiella oxytoca*," *Molecular Microbiology*, 2(4):443–454 (1988).

Basnayake et al., "A gene from *Alcaligenes denitrificans* that confers albicidin resistance by reversible antibiotic binding," *Microbiology*, 141:551–560 (1995).
Birch et al., "Stable albicidin resistance in *Escherichia coli* involves an altered outer–membrane nucleoside uptake system," *Journal of General Microbiology*, 136:51–58 (1990); and .
Zhang et al., "Biocontrol of sugar cane leaf scald disease by an isolate of *Pantoea dispersa* which detoxifies albicidin phytotoxins," *Letters in Applied Microbiology*, 22:132–136 (1996).

* cited by examiner

*Primary Examiner*—David T. Fox
*Assistant Examiner*—Ashwin D. Mehta
(74) *Attorney, Agent, or Firm*—Akin, Gump, Strauss, Hauer & Feld, L.L.P.

(57) ABSTRACT

A method of substantially reducing or inhibiting the development of leaf scald disease in a plant or stalk thereof, said method comprising the step of administering an albicidin detoxification enzyme to the plant or stalk thereof.

There is also provided a method of generating a transgenic plant substantially resistant to albicidin and leaf scald disease including the steps of introducing and expressing a nucleotide sequence encoding albicidin detoxification enzyme into a plant, plant part or plant cell, and growing the plant, plant part or plant cell to generate the transgenic plant.

There is further provided a method of substantially reducing or inhibiting the development of leaf scald disease in a plant or stalk thereof, said method comprising the step of administering to the plant or stalk thereof a bacterium which extracellularly produces albicidin detoxification enzyme.

There is further provided an isolated albicidin detoxification enzyme capable of irreversibly inactivating albicidin as well as an isolated nucelotide sequence encoding an albicidin detoxification enzyme.

18 Claims, 19 Drawing Sheets

MDKSDLTETSRIKHGEEAFDVTLLQVKGATRCILFAAGLSGSPLRHLELLQTFARHGVSV 60

VAPHFERLTSPVPTRAELLERCQRLARAQNEFCSGYASVTGVGHSLGSVILLNAGAIAM 120

TSAGESVVFAGDRMLHRLILLAPPADFFQAPSALAAVNVPVHIWAGEKDSLTPPSQACFL 180

KQALEGYTQTYLCVMEEAGHFTFMNTLPPQVTDSHPSREAFLLDLGENIARLVTD 235

Fig. 3A

```
-154   ATGCAGAGGGCTCAATGACGTTTCATCCCAATGTCCTGACCAGTCATAA  -105
       ------+---------+---------+---------+---------+----
       TACGTCTCCCCGAGTTACTGCAAAGTAGGGTTACAGGACTGGTCAGTATT

-104   TTCACCAAGCCGAGTTTGCTGTGTGGCAGAATGGCATCCAACGCGTAAA  -55
       ------+---------+---------+---------+---------+----
       AAGTGGTTCGGCTCCAAACGACACACCGTCTTACCGTAGGTTGCGCATTT

5'-TTAAGCGGGATCCGT
                                                         *
-54    GGTGGGCGAGAGCCTGTTAATATTTTTGACAATCGGTTAAGCGGGATGCGT  -5
       ------+---------+---------+---------+---------+----
       CCACCGCTCTCGGACAATTATAAAAACTGTTAGCCAATTCGCCCTACGCA

TTTGATGGAC-3'

-4     TTTGATGGACAAAAGTGATCTCACGGAAACGTCTCGGATCAAACATGGGG  45
       ------+---------+---------+---------+---------+----
       AAACTACCTGTTTTCACTAGAGTGCCTTTGCAGAGCCTAGTTTGTACCCC
```

Fig. 3B

```
 46  AAGAGGCGTTTGACGTCACCTTATTGCAGGTTAAGGGGCGACGCGCTGT   95
     ----+----|----+----|----+----|----+----|----+----
     TTCTCCGCAAACTGCAGTGGAATAACGTCCAATTCCCCGCTGCGCGACA

96  ATCCTTTTTGCTGCGGGGCTGAGCGGCAGTCCGCTGCGCCATCTTGAACT   145
     ----+----|----+----|----+----|----+----|----+----
     TAGGAAAAACGACGCCCCGACTCGCCGTCAGGCGACGCGGTAGAACTTGA

146  TCTCCAGACCTTTGCCCGCCATGGCGTTTCCGTTGTCGCGCCACACTTTG   195
     ----+----|----+----|----+----|----+----|----+----
     AGAGGTCTGGAAACGGGCGGTACGCAAAGGCAACAGCGCGGTGTGAAAC

196  AACGGTTGACCTCACCCGTGCCCACCAGAGCTGAATTACTGGAACGCTGC   245
     ----+----|----+----|----+----|----+----|----+----
     TTGCCAACTGGAGTGGGCACGGGTGGTCTCGACTTAATGACCTTGCGACG

246  CAGCGGGCTTGCGCGGGCTCAGAATGAATTTTGTAGCGGTTATGCGTCGGT   295
     ----+----|----+----|----+----|----+----|----+----
     GTCGCCGAACGCGCCCGAGTCTTACTTAAAACATCGCCAATACGCAGCCA
```

Fig. 3C

```
296  TACCGGTGTTGGCCACTCCCCTGGGTAGCGTGATTTATTGCTGAATGCCG  345
     ----+----|----+----|----+----|----+----|----+----|
     ATGGCCACAACCGGTGAGGGACCCATCGCACTAAAATAACGACTTACGGC

346  GGGCTATAGCGATGACAAGCGCAGGGGAATCGGTTGTTTTCGCCGGCGAC  395
     ----+----|----+----|----+----|----+----|----+----|
     CCCGATATCGCTACTGTTCGCGTCCCCTTAGCCAACAAAAGCGGCCGCTG

396  CGGATGTTGCATCGACTTATTTTACTGGCACCGCCCCGCCGATTTTTCCA  445
     ----+----|----+----|----+----|----+----|----+----|
     GCCTACAACGTAGCTGAATAAAATGACCGTGGCGGCGGCTAAAAAAGGT

446  GGCTCCGTCTGCGCTGGCAGCGGTGAACGTACCTGTTCACATCTGGGCAG  495
     ----+----|----+----|----+----|----+----|----+----|
     CCGAGGCAGAGACGCGACCGTCGCCACTTGCATGGACAAGTGTAGACCCGTC

496  GTGAAAAGGACAGCCTGACGCCCCGTCCCAGGCCTGCTTTCTTAAACAG  545
     ----+----|----+----|----+----|----+----|----+----|
     CACTTTTCCTGTCGGACTGCGGGGCAGGGTCCGGACGAAAGAATTTGTC
```

FIG. 3D

```
546  GCACTGGAGGGTTACACGGCAGAGACTTATCTCTGTGTGATGGAAGAGGCCGG
     ----+----|----+----|----+----|----+----|----+----|  595
     CGTGACCTCCCAATGTGCCGTCTGAATAGAGACACACTACCTTCTCCGGCC

596  GCATTTACCTTCATGAATACCCTTGCCTCCGCAGGTAACCGATTCACATC
     ----+----|----+----|----+----|----+----|----+----|  645
     CGTAAAATGGAAGTACTTATGGAACGGAGGCGTCCATTGGCTAAGTGTAG

646  CGTCGCGGGAGGCCTTTCTTTTAGATTTGGGCGAAAACATAGCCCGGCTG
     ----+----|----+----|----+----|----+----|----+----|  695
     GCAGCGCCCTCCGGAAAGAAAATCTAAACCCGCTTTTGTATCGGGCCGAC

696  GTGACTGATTAGCACAGAGGGCGGGGCGATGAGATTTTTGCAGGATAAC
     ----+----|----+----|----+----|----+----|----+----|  745
     CACTGACTAATCGTGTCTCCCGCCCCGCTACTCTAAAAACGTCCCTATTG
```

Fig. 3E

```
       CTCTTCCAGCTGATACGATTCAATCATACTCATCAAAAGCATCATTTCAT
746    --------+---------+---------+---------+---------+    795
       GAGAAGGTCGACTATGCTAAGTTAGTATGAGTAGTTTTCGTAGTAAAGTA

3'-GAGAAGGTCGACTATGCTAAGTTAG-5'

CCTGTCTTAGGGGCTATTGTGAAACAGAAATCGGCCCTATAGTGAGTCGT
796    --------+---------+---------+---------+---------+    845
       GGACAGAATCCCCGATAACACTTTGTCTTTAGCCGGGATATCACTCAGCA

ATTACGCCCGCTCGAA
846    --------+-------    861
       TAATGCGGGCGAGCTT
```

Fig. 3F

```
            34                          49
A.   L FAAGLSGSPLRHLEL
                 •      •  •  •
       • •     • •      •  •  •
B.   MYDKYFSR EELARLP L
      • ••    • •    • •   • •
     • • • •  • • •  • •  • • • • • • •
C.   MYDRWFSQQE LQVLPF
```

Fig. 4

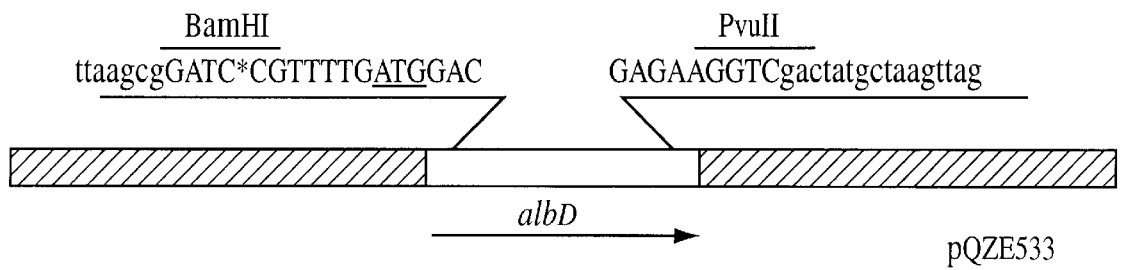
Fig. 7A
```
           THROMBIN
    ┌ L  V  P  R ▼ G     S ┐  V    L    M   D
      ctg gtt ccg cgt gGA TCC GTT TTG ATG GAC..................TAG........
```
Fig. 7B
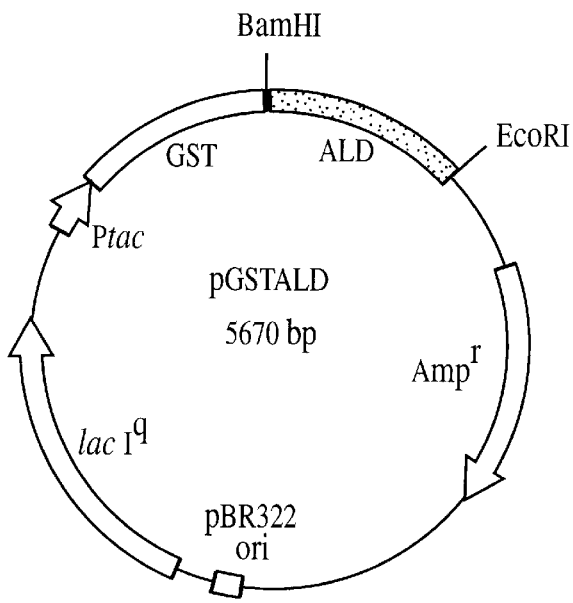
Fig. 7C

CONTROL OF LEAF SCALD DISEASE

FIELD OF THE INVENTION

THIS INVENTION relates to the control of leaf scald disease and the inactivation of the phytotoxin albicidin in plants and particularly in sugarcane.

BACKGROUND ART

Leaf scald is a major disease of sugarcane which occurs in more than 50 countries (Chen et al., 1991, Report of the Taiwan Sugar Research Institute 0 (132), 19–27; Comstock and Shine, 1992, Plant Disease 76 (4), 426; Grisham et al., 1993, Plant Disease, 77 (5), 537; Irvine et al., 1993, Plant Disease, 77 (8), 846). The causal agent has been identified as *Xanthomonas albilineans*. *X. albilineans* produces a family of antibiotics and phytotoxins called albicidins. Albicidins selectively block DNA replication in bacteria and chloroplasts. Albicidin is the subject of U.S. Pat. No. 4,525,354. Mutants of *X. albilineans* which do not produce albicidins do not produce chlorotic or any systemic disease symptoms in inoculated sugarcane (Birch and Patil, 1987, Physiol. Molec. Plant Pathol., 30, 199–206). This indicates that albicidins are responsible for the chlorotic symptoms on *X. albilineans* infected sugarcanes, and play an important role in sugarcane leaf scald disease.

Two different mechanisms of albicidin resistance have been identified in bacteria. One mechanism involves the loss of cell permeability in some *Escherichia coli* mutants to albicidin (Birch et al., 1990 J. Gen. Microbiol., 136, 51–58). The other involves the inactivation of albicidin by the formation of a reversible protein-albicidin binding complex. This formation of a reversible binding complex has been shown in *Klebsiella oxytoca* to involve the albicidin resistance protein AlbA (Walker et al., 1988, Molec. Microbiol., 2 (4), 443–454) and in *Alcaligenes denitrificans* (Basnayake and Birch, 1995, Microbiology, 141) to involve the albicidin resistance protein AlbB. Unfortunately, however, these proteins do not irreversibly inactivate albicidin and consequently are not considered to be efficacious candidates for controlling leaf scald disease.

Leaf scald disease is an economically important disease and causes a large commercial loss in the sugarcane industry where susceptible cultivars are grown. As a result, ways of effectively combatting the disease are of great economic significance. For example, leaf scald resistance in plants is an essential requirement for every commercial Australian sugarcane variety. Selection for this resistance has unavoidably had a significant impact on the breeding program by reducing the value of some desired crosses and leading to the rejection of what would be otherwise outstanding new varieties. It takes about 10 years for breeding a new sugarcane variety and rejection of one variety in the final stage of the breeding program would cost the industry around $1 million. The recent development of a sugarcane genetic transformation system (Franks and Birch, 1991, Aust. J. Pit. Physiol., 18, 471–480); Bower and Birch, 1992, Plant J., 2, 409–416) has enabled the molecular improvement of sugarcane varieties and provided a supplementary mechanism to the conventional breeding programs.

SUMMARY OF THE INVENTION

The current invention arises from the unexpected discovery of an albicidin detoxification enzyme produced from a bacterium. It was further found that the albicidin detoxification enzyme was secreted extracellularly. Unlike the previously described albicidin binding protein AlbA and AlbB, inactivation of albicidin by the enzyme was irreversible in the sense that albicidin toxin activity was not restored upon protein denaturing treatment such as boiling. The bacterium that produced the albicidin detoxifying enzyme was identified as a strain of *Erwinia herbicola* also known as *Pantoea dispersa*.

It is therefore an object of the invention to provide an albicidin detoxification enzyme for use in treating plants infected with leaf scald disease or reducing the probability of plants becoming infected with leaf scald disease.

It is a further object of the invention to provide a DNA sequence encoding an albicidin detoxification enzyme for the generation of transgenic plants and plant cells which are substantially resistant to albicidin such that resistance to leaf scald disease is substantially effected. Thus, it is yet another object to provide a transgenic plant substantially resistant to leaf scald disease.

Accordingly, in one aspect of the invention, there is provided an albicidin detoxification enzyme.

The term "albicidin detoxification enzyme" as used herein refers to a protein which catalyses the conversion of an albicidin to one or more non-toxic products wherein subsequent removal or destruction of the protein does not result in restoration of the albicidin from the non-toxic product(s). Accordingly, a protein being an albicidin detoxification enzyme may be distinguished from a protein which inactivates albicidin merely by binding reversibly thereto (eg. AlbA and AlbB) by subjecting a mixture of the protein and an albicidin to a protein denaturation step such as boiling. If the protein is an albicidin detoxification enzyme, then albicidin activity lost or reduced upon treatment with the protein is not restored by protein denaturation. Such "enzymatic detoxification" is highly advantageous because it provides a more effective and substantially permanent protection against albicidin toxicity than other mechanisms mentioned heretofore which are reversed upon denaturation of a molecule which merely binds reversibly to albicidin. It will also be appreciated that enzymatic detoxification may be highly beneficial in that an albicidin detoxification enzyme can progressively detoxify multiple albicidin molecules in contrast to albicidin binding molecules which merely bind albicidin without catalytic breakdown or modification thereof.

The albicidin detoxification enzyme is preferably a hydrolase. A suitable albicidin detoxification enzyme includes, but is not limited to, an AlbD polypeptide comprising the sequence of amino acids as shown in FIG. 3A (SEQ ID NO:1).

Alternatively, the AlbD polypeptide is an "AlbD polypeptide homolog". Thus, the invention contemplates polypeptides which are functionally similar to the AlbD polypeptide. Such polypeptides may contain conservative amino acid substitutions compared to the AlbD polypeptide of FIG. 3A (SEQ ID NO:1).

The AlbD polypeptide homolog may be obtained from any suitable organism such as a eukaryotic cell including a yeast cell. Preferably, the AlbD polypeptide homolog is obtained from a bacterium such as, for example, an Erwinia or Pantoea strain. Alternatively, the AlbD polypeptide or polypeptide homolog thereof may be obtained by first isolating a DNA sequence encoding a polypeptide of the AlbD type as for example described hereinafter.

An albicidin detoxification enzyme of the invention may be prepared by a procedure including the steps of:

(a) ligating a DNA sequence encoding an albicidin detoxification enzyme or biological fragment thereof into a suitable expression vector to form an expression construct;

(b) transfecting the expression construct into a suitable host cell;
(c) expressing the recombinant protein; and
(d) isolating the recombinant protein.

As used in this specification, an expression construct is a nucleotide sequence comprising a first nucleotide sequence encoding a polypeptide, wherein said first sequence is operably linked to regulatory nucleotide sequences (such as a promoter and a termination sequence) that will induce expression of said first sequence. Both constitutive and inducible promoters may be useful adjuncts for expression of an albicidin detoxification enzyme according to the invention. An expression construct according to the invention may be a vector, such as a plasmid cloning vector. A vector according the invention may be a prokaryotic or a eukaryotic expression vector, which are well known to those of skill in the art.

Suitable host cells for expression may be prokaryotic or eukaryotic. One preferred host cell for expression of a polypeptide according to the invention is a bacterium. The bacterium used may be *Escherichia coli.*

The recombinant protein may be conveniently prepared by a person skilled in the art using standard protocols as for example described in Sambrook et al. (1989, Second Edition, Cold Spring Harbor Laboratory Press, 1989, in particular Sections 16 and 17).

Further, there is provided a method of substantially reducing or inhibiting the development of leaf scald disease in a plant, said method comprising the step of administering an albicidin detoxification enzyme to the plant.

In this case, the plant is preferably sugarcane and other plants susceptible to leaf scald disease.

The albicidin detoxification enzyme may be combined with other agents and may be administered by any suitable method. A suitable method includes soaking of stalks or setts of the plant prior to planting, and infiltration or injection of the albicidin detoxification enzyme into the plant.

In another aspect, the invention resides in a nucleotide sequence encoding an albicidin detoxification enzyme. The nucleotide sequence may comprise a nucleotide sequence encoding albD of *P. dispersa*. Accordingly, the nucleotide sequence may comprise the entire sequence of nucleotides as shown in FIG. 3B (SEQ ID NO:2). Alternatively, the nucleotide sequence may comprise nucleotide 1 through nucleotide 704 of FIG. 3B (such nucleotide sequence 1 through 704 being identified as SEQ ID NO:3).

The term "nucleotide sequence" as used herein designates mRNA, RNA, cRNA, cDNA or DNA.

The invention also provides homologs of the albD nucleotide sequences of the invention as described above. Such "albD homologs", as used in this specification include all nucleotide sequences encoding sub-sequences of this polypeptide which confer albicidin resistance. In this regard, codon sequence redundancy means that changes can be made to a nucleotide sequence without affecting the corresponding polypeptide sequence.

The homologs of the invention further include nucleotide sequences encoding polypeptides that have the same functional characteristics as the AlbD polypeptides of the invention. One of skill in the art will appreciate that conservative amino acid substitutions can be made in a AlbD polypeptide according to the invention and that such substituted polypeptides will retain the functional characteristics of an AlbD polypeptide according to the invention.

The homologs of the invention further comprise nucleotide sequences that hybridize with an albD nucleotide sequence of the invention under stringent conditions. Suitable hybridization conditions are discussed below.

The albD homologs of the invention may be prepared according to the following procedure:

(i) designing primers which are preferably degenerate which span at least a fragment of a nucleotide sequence of the invention; and (ii) using such primers to amplify, via PCR techniques, said at least a fragment from a nucleic acid extract obtained from a suitable host. In this regard, the suitable host is preferably a bacterium such as, for example, an Erwinia or Pantoea strain.

"Hybridization" is used here to denote the pairing of complementary nucleotide sequences to produce a DNA—DNA hybrid or a DNA-RNA hybrid. Complementary base sequences are those sequences that are related by the base-pairing rules. In DNA, A pairs with T and C pairs with G. In RNA, U pairs with A and C pairs with G.

Typically, nucleotide sequences to be compared by means of hybridization are analyzed using dot blotting, slot blotting, or Southern blotting. Southern blotting is used to determine the complementarity of DNA sequences. Northern blotting determines complementarity of DNA and RNA sequences. Dot and Slot blotting can be used to analyze DNA/DNA or DNA/RNA complementarity. These techniques are well known by those of skill in the art. Typical procedures are described in CURRENT PROTOCOLS IN MOLECULAR BIOLOGY (Ausubel, et al., eds.) (John Wiley & Sons, Inc. 1995) at pages 2.9.1 through 2.9.20. Briefly, for Southern blotting, DNA samples are separated by size using gel electrophoresis. The size-separated DNA samples are transferred to and immobilized on a membrane (typically, nitrocellulose) and the DNA samples are probed with a radioactive, complementary nucleic acid. In dot blotting, DNA samples are directly spotted onto a membrane (nitrocellulose or nylon). In slot blotting, the spotted DNA samples are elongated. The membrane is then probed with a radioactive complementary nucleic acid.

A probe is a biochemical labeled with a radioactive isotope or tagged in other ways for ease in identification. A probe is used to identify a gene, a gene product or a protein. Thus a nucleotide sequence probe can be used to identify complementary nucleotide sequences. An mRNA probe will hybridize with its corresponding DNA gene.

Typically, the following general procedure can be used to determine hybridization under stringent conditions. A nucleotide according to the invention (such as albD or a subsequence thereof) will be immobilized on a membrane using one of the above-described procedures for blotting. A sample nucleotide sequence will be labeled and used as a "probe." Using procedures well known to those skilled in the art for blotting described above, the ability of the probe to hybridize with a nucleotide sequence according to the invention can be analyzed.

One of skill in the art will recognize that various factors can influence the amount and detectability of the probe bound to the immobilized DNA. The specific activity of the probe must be sufficiently high to permit detection. Typically, a specific activity of at least $10^8$ dpm/$\mu$g is necessary to avoid weak or undetectable hybridization signals when using a radioactive hybridization probe. A probe with a specific activity of $10^8$ to $10^9$ dpm/$\mu$g can detect approximately 0.5 pg of DNA. It is well known in the art that sufficient DNA must be immobilized on the membrane to permit detection. It is desirable to have excess immobilized DNA and spotting 10 $\mu$g of DNA is generally an acceptable amount that will permit optimum detection in most circumstances. Adding an inert polymer such as 10% (w/v) dextran sulfate (mol. wt. 500,000) or PEG 6000 to the hybridization solution can also increase the sensitivity of the hybridization. Adding these polymers has been known to increase the hybridization signal. See Ausubel, supra, at p 2.10.10.

To achieve meaningful results from hybridization between a first nucleotide sequence immobilized on a membrane and a second nucleotide sequence to be used as a hybridization probe, (1) sufficient probe must bind to the immobilized DNA to produce a detectable signal (sensitivity) and (2) following the washing procedure, the probe must be attached only to those immobilized sequences with the desired degree of complementarity to the probe sequence (specificity).

"Stringency," as used in this specification, means the condition with regard to temperature, ionic strength and the presence of certain organic solvents, under which nucleic acid hybridizations are carried out. The higher the stringency used, the higher degree of complementarity between the probe and the immobilized DNA.

"Stringent conditions" designates those conditions under which only nucleotide sequences that have a high frequency of complementary base sequences will hybridize with each other.

Exemplary stringent conditions are (1) 0.75 M dibasic sodium phosphate/0.5 M monobasic sodium phosphate/1 mM disodium EDTA/1% sarkosyl at about 42° C. for at least about 30 minutes, (2) 6.0M urea/0.4% sodium lauryl sulfate/ 0.1% SSC (20×; 3 M NaCl, 0.3 M Na$_3$citrate-2H$_2$O, pH7.0) at about 42° C. for at least about 30 minutes, (3) 0.1×SSC/ 0.1% SDS at about 68° C. for at least about 20 minutes, (4) 1×SSC/0.1% SDS at about 55° C. for about one hour, (5) 1×SSC/0.1% SDS at about 62° C. for about one hour, (6) 1×SSC/0.1% SDS at about 68° C. for about one hour, (7) 0.2×SSC/0.1% SDS at about 55° C. for about one hour, (8) 0.2×SSC/0.1% SDS at about 62° C. for about one hour, and (9) 0.2×SSC/0.1% SDS at about 68° C. for about one hour. See, e.g. CURRENT PROTOCOLS IN MOLECULAR BIOLOGY (Ausubel, et al., eds.) (John Wiley & Sons, Inc. 1995), pages 2.10.1–2.10.16 of which are hereby incorporated by reference and Sambrook, et al., MOLECULAR CLONING. A LABORATORY MANUAL (Cold Spring Harbor Press, 1989) at §§1.101–1.104.

Stringent washes are typically carried out for a total of about 20 minutes to about 60 minutes. In certain instances, more than one stringent wash will be required to remove sequences that are not highly similar to albD or a subsequence thereof. Typically, two washes of equal duration, such as two 15 or 30 minute washes, are used. One of skill in the art will appreciate that other longer or shorter times may be employed for stringent washes to ensure identification of sequences similar to albD.

While stringent washes are typically carried out at temperatures from about 42° C. to about 68° C., one of skill in the art will appreciate that other temperatures may be suitable for stringent conditions. Maximum hybridization typically occurs at about 20 to about 25° C. below the $T_m$ for DNA—DNA hybrids. It is well known in the art that $T_m$ is the melting temperature, or temperature at which two nucleotide sequences dissociate. Methods for estimating $T_m$ are well known in the art. See, e.g. Ausubel, supra, at page 2.10.8. Maximum hybridization typically occurs at about 10 to about 15° C. below the $T_m$ for DNA-RNA hybrids.

Other typical stringent conditions are well-known in the art. One of skill in the art will recognize that various factors can be manipulated to optimize the specificity of the hybridization. Optimization of the stringency of the final washes can serve to ensure a high degree of hybridization between the albD gene (or subsequence thereof) and other similar nucleotide sequences.

In a typical hybridization procedure, DNA is first immbolized on a membrane such as a nitrocellulose membrane or a nylon membrane. Procedures for DNA immobilization on such membranes are well known in the art. See, e.g., Ausubel, supra at pages 2.9.1–2.9.20. The membrane is prehybridized at 42° C. for 30–60 minutes in 0.75 M dibasic sodium phosphate/0.5 M monobasic sodium phosphate/1 mM disodium EDTA/1% sarkosyl. Membranes are then hybridized at 42° C. in ACES hybridization solution (Life Technologies, Inc., Gaithersburg, Md.) containing labeled probe for one hour. Next, membranes are subjected to two high stringency 10 minute washes at 42° C. in 0.75 M dibasic sodium phosphate/0.5 M monobasic sodium phosphate/1 mM disodium EDTA/1 % sarkosyl. Following this, the membranes are washed with 2×SSC. at room temperature, to remove unbound probe.

In another typical hybridization procedure, DNA immobilized on a membrane is hybridized overnight at 42° C. in prehybridization solution. Following hybridization, blots are washed with two stringent washes, such as 6.0M urea/0.4% sodium lauryl sulfate/0.1% SSC. at 42° C. Following this, the membranes are washed with 2×SSC. at room temperature.

Autoradiographic techniques for detecting radioactively labeled probes bound to membranes are well known in the art.

There is also provided a method of generating a transgenic plant substantially resistant to albicidin and leaf scald disease, said method including the steps of introducing and expressing a nucleotide sequence encoding albicidin detoxification enzyme into a plant, plant part or plant cell, and growing the plant, plant part or plant cell to generate the transgenic plant.

The invention also comprises a method of generating a transgenic plant substantially resistant to albicidin and leaf scald disease, said method including the steps of introducing into a plant, or plant part or cell thereof a vector comprising a nucleotide sequence encoding an albicidin detoxification enzyme wherein said nucleotide sequence is operably linked to one or more regulatory nucleotide sequences and growing said plant or plant part or cell thereof to generate the transgenic plant.

The nucleotide sequence encoding the albicidin detoxification enzyme may include any of the sequences described above. The nucleotide sequence may comprise the entire sequence of nucleotides as shown in FIGS. 3B–3F (SEQ ID NO:2). Preferably, the nucleotide sequence comprises nucleotide 1 through nucleotide 704 of FIGS. 3B–3F (SEQ ID NO:3).

The plant, plant part or plant cell may be obtained from any suitable plant which could be infected with leaf scald disease. Preferably, the plant, plant part or plant cell is obtained from a sugarcane variety.

In another aspect, the invention provides a transgenic plant substantially resistant to albicidin and leaf scald disease, said plant comprising a nucleotide sequence encoding an albicidin detoxification enzyme wherein said sequence is operably linked to one or more regulatory nucleotide sequences.

Preferably, the nucleotide sequence is stably incorporated within cells of said plant.

Of course, it will be appreciated that if the albicidin detoxification enzyme requires transportation to a specific cellular compartment in order to effect resistance to albicidin, such transportation may be effected by construction of a translational fusion comprising the albicidin detoxification enzyme fused in frame with a DNA sequence encoding a transit peptide. Such transit peptides are well known in the art and may include, for example, a plastid transit peptide such as the maize waxy transit peptide as for example described in an article by Klösgen and Weil (1991, Molec. Gen. Genet., 225, 297–304) which is hereby incorporated by reference. This transit peptide has been used in targeting a range of proteins to the plastids of a range of plant species, for example in locating the NPT II protein to tobacco chloroplasts (Van den Broeck et al., 1985, ) and in locating GUS protein into chloroplasts of potato plants (Klösgen and Weil, 1991, Nature, 313, 358–363).

A vector according to the invention may be a prokaryotic or a eukaryotic expression vector, which are well known to those of skill in the art. Such vectors may contain one or more copies of the nucleotide sequences according to the invention.

Regulatory nucleotide sequences which may be utilized to regulate expression of the nucleotide sequence encoding the albicidin detoxification enzyme include, but are not limited to, a promoter, an enhancer, and a transcriptional terminator. Such regulatory sequences are well known to those of skill in the art.

Suitable promoters which may be utilized to induce expression of the nucleotide sequences of the invention include constitutive promoters and inducible promoters. A particularly preferred promoter which may be used to induce such expression includes the $p_{EMU}$ monocots promoter as described for example in U.S. Pat. No. 5,290,924 (Last et al), and the plant ubiquitin promoter $p_{UBI}$ as described for example in EP342926 (Quail).

Any suitable transcriptional terminator may be used which effects termination of transcription of a nucleotide sequence in accordance with the invention. Preferably, the nopaline synthase (NOS) terminator, as for example disclosed in U.S. Pat. No. 5,034,322, is used as the transcription terminator.

The vector may also include a selection marker such as an antibiotic resistance gene which can be used for selection of suitable transformants. Examples of such resistance genes include the nptil gene which confers resistance to the antibiotics kanamycin and G418 (Geneticin®) and the hph gene which confers resistance to the antibiotic hygromycin B.

A nucleotide sequence or vector according to the invention may be introduced into a plant, or plant part, or cell thereof using any suitable method including transfection, projectile bombardment, electroporation or infection by *Agrobacterium tumefaciens*.

It will of course be appreciated that gene transplacement by homologous recombination may also be used to effect the generation of suitable transgenic plants. Such methods are well known to persons of skill in the art.

In yet another aspect of the invention, there is provided a bacterium which can produce an albicidin detoxification enzyme for use in treating plants infected with leaf scald disease and/or reducing the probability of plants becoming infected with leaf scald disease.

The bacterium may be any suitable strain derived from a naturally occurring strain capable of producing albicidin detoxification enzyme when selected by procedures outlined in the preferred embodiment. A suitable bacterium may be a strain of *Erwinia herbicola* such as *E. herbicola* SB1403 (also known as *Pantoea dispersa* SB1403). A description of *E. herbicola* SB1403 is given in the preferred embodiment. This strain has been deposited with the Australian Government Analytical Laboratories on Apr. 11, 1995 with the accession number N95/21834.

Alternatively, the organism may be any suitable strain capable of expressing extracellularly a nucleotide sequence encoding the albicidin detoxification enzyme as herein described. Suitable strains include *E. coli* and suitable soil or plant commensal bacteria harbouring a copy of the gene encoding albicidin detoxification enzyme.

There is also provided a method of substantially reducing or inhibiting the development of leaf scald disease in a plant or stalk thereof, said method comprising the step of administering to the plant or stalk thereof a bacterium which extracellularly produces albicidin detoxification enzyme. The method may include as the biocontrol agent a strain of *P. dispersa* or a suitable host expressing a cloned sequence encoding albicidin detoxification enzyme.

The strain may be administered by any suitable method including spraying on the foliage. Other examples or administration include the dripping of cultures onto base cutters or cutter-planters, or through spray nozzles directed at freshly cut stubble. The biocontrol agent may be combined with one or more other agents which facilitate its operation or perform additional tasks. Other agents may include fungicides.

BRIEF DESCRIPTION OF THE DRAWINGS

FIG. 3A designates the predicted polypeptide sequence encoded by the albD gene (SEQ ID NO:1);

FIGS. 3B–3F show the nucleotide sequence of the albD gene (SEQ ID NO:2);

FIG. 4 refers to a best matched comparison of amino acid sequences encoded by the albD gene product (SEQ ID NO:4) and the proteins respectively encoded by the *A. denitrificans* albB gene (SEQ ID NO:5) and by the *K. oxytoka* albA gene (SEQ ID NO:6);

FIG. 7A illustrates a 790 base pair albD structural gene fragment which was amplified using PCR and specific flanking oligonucleotide primers SEQ ID NO:7 and SEQ ID NO:8, respectively;

FIG. 7B illustrates the position of the thrombin cleavage site upstream of the predicted initiation codon of albD (peptide identified as SEQ ID NO:9; nucleotide base identified as SEQ ID NO:10);

FIG. 7C refers to a map of GST-albD gene fusion construct pGSTALD;

PREFERRED EMBODIMENTS

EXAMPLE 1

Expression of Albicidin Detoxification Enzyme from *Pantoea dispersa* in Transgenic Sugarcane

MATERIALS AND METHODS

Bacteria and cultivation. The bacterial strains and plasmids used in this work are listed in TABLE 1. *E. coli* strain DH5α was used as albicidin activity indicator strain and also as the host strain for DNA cloning and subcloning; *X. albilineans* strain XA3 isolated from diseased sugarcane from Queensland, Australia was used as albicidin production strain; the different albicidin-resistant ($Alb^r$) isolates isolated from *X. albilineans* infected sugarcanes were listed in TABLE 2. *E. coli* strains were grown and maintained in LM medium (Miller, 1972, Experiments in Molecular Genetics, Cold Spring Harbour, N.Y.: Cold Spring Harbor Laboratory Press), the others in SP medium (Birch and Patil, 1985, J. Gen. Microbiol., 131, 1069–1075). Except for *E. coli* strains that were usually grown at 37° C., all the other strains and isolates were grown in 28° C. Broth cultures aerated by shaking at 200 rpm on an orbital shaker.

Isolation of bacteria. *X. albilineans* infected sugarcane samples were collected from Eight Mile Plains, Queensland, Australia. These samples were surface sterilised by 70% ethanol and then segmented into small pieces. The pieced samples were suspended in sterilised water and shaken in a reciprocal shaker for 1 h before spreading over SP agar plates (Birch and Patil, 1985, J. Gen. Microbiol., 131, 1069–1075). The colonies which appeared were collected based on morphology for further analysis.

Preparation of albicidin. Albicidins produced in culture by *X. albilineans* were purified as described previously (Birch and Patil, 1985, J. Gen. Microbiol., 131, 1069–1075; and Birch et al., 1990, J. Gen. Microbiol., 136, 51–58). Unless stated otherwise, the mixture of albicidins obtained after HW-40(s) chromatography was used in experiments reported here.

Albicidin bioassay. Albicidin was quantified as described previously (Birch and Patil, 1985, J. Gen. Microbiol., 131, 1069–1075).

Inactivation of albicidin by intact bacterial cells. Actively growing bacterial culture with $OD_{600}$ equal to about 1.5 was added to equal volume of SP or LM liquid broth containing albicidin with a final concentration of 1000 units/mL. Samples were removed at intervals and placed on ice or boiled for 5 min. After reaction, samples were centrifuged and supernatants were collected. For unboiled treatment, supernatants were exposure to UV light for 10 min before bioassay.

Cell free extract preparation. Bacterial isolates were inoculated in 100 ml of SP liquid medium and grown for 24 h with shaking at 28° C. Cells were harvested by centrifugation at 11020×g for 10 min and washed in TEMM buffer (10 mM Tris pH 7.45, 10 mM EDTA, 10 mM $MgCl_2$ and 2 mM β-mercaptoethanol). The cells were resuspended in 2 ml TEMM buffer and disrupted by sonification on ice with a microprobe (model 250, Branson Ultrasonic Corporation, Danbury, Conn.) at 50% duty cycle and an output setting of 3. Sonification was performed for 3 min of 8 second burst periods followed by 8 second rest periods. Cell disruption was confirmed by using phase contrast microscopy. Cell debris was removed by centrifugation at 11020×g for 20 min. The protein concentration in the cell extracts was then determined by dye reagent method (Bradford, 1976, Analytical Biochemistry, 72, 248–254) using bovine serum albumin as standard control.

Taxonomic identification method. Gram reaction was tested by using KOH method (Suslow et al., 1982, Phytopathology, 72, 917–918). Utilisation of different carbon sources were tested by using BIOLOG GN Microplate™ (Biolog Inc.). Oxidation fermentation assay was performed by using Hugh and Leifson (HL) test (Collins and Lyne, 1984, Microbiological Methods, 5th Ed. London, Butterworths).

Plant material and bacterial inoculation. Sugarcane variety Q44 was used in all biocontrol experiments, single-node cuttings from *X. albilineans* free healthy sugarcane plants were potted in PH1 contamination greenhouse for about two months before inoculation. A decapitation method described previously (Birch and Patil, 1983, Phytopathology, 73, 1368–1374) was used for inoculation of *X. albilineans* and *E. herbicola* strains. The actively growing bacteria (2 days culture of *X. albilineans* strains and 24 h culture of *E. herbicola* strains) were centrifuged for 1 min at 14000 rpm, resuspended and diluted with sterilised water to relevant concentrations, and kept on ice until inoculation.

Cloning and sequencing of the albD gene. A cosmid genomic library of *E. herbicola* SB1403 was constructed in *E. coli* DH5α by partial digestion of the SB1403 DNA with BamHI restriction endonuclease and ligation into the BamHl site of the cosmid cloning vector pLAFR3. Albicidin resistant recombinant clones were selected by patching the recombinant cosmid clone transformants onto LB agar medium containing 10 μg/mL Tc and 20 u/mL albicidin. T6 phage sensitivity was confirmed by cross streaking. Subcloning into pBluescript II SK(+) was carried out according to routine techniques (Sambrook et al., 1989. NY: Molecular Cloning: A Laboratory Manual, 2nd Ed. Cold Spring Harbour Laboratory.).

$Alb^r$ clone pQZE533 and four ExoIII deletion sub-clones (pQZE456, pQZE457, pQZE540 and pQZE560) were used to obtain the complete DNA sequence from both strands of the cloned albD gene. DNA sequencing was based on the dideoxynucleotide chain termination method of (Sanger et al., 1977, PNAS USA, 74, 5463–5467). The PRISM™ Ready Reaction DyeDeoXy™ Terminator Cycle Sequencing Kit was from Applied Biosystems.

Sited directed mutagenesis of albD gene in *E. herbicola* SB1403. A 326 bp HincII-StuI fragment, constituting an internal segment of the albD gene of *E. herbicola* SB1403 was ligated into the suicide vector pJP5603. The ligation products were used to transform *E. coli* JM109 (λpir). A recombinant clone pJPAldHS was identified by restriction enzyme digestion agarose gel electrophoresis. It was transferred into the mobilising strain S17-1 (λpir), and mobilised into *E. herbicola* SB1403rif. Exconjugant colonies were selected on SP agar medium containing 50 μg/mL kanamycin and 50 μg/mL rifampicin, and tested for albicidin detoxification enzyme production.

PCR amplification and modification of albD gene. A plasmid clone pQZE533 containing albD gene was used as a template for PCR amplification. Two oligonucleotide primers were synthesised corresponding to the 5' and 3' flanking regions of albD structural gene. The 5' and 3' primers were (5'-TTMG CGGGA TCCGT TTTGA TGGAC-3') (SEQ ID NO:7) and (5'-GATTG MTCG TATCA GCTGG MGAG-3') (SEQ ID NO:8), respectively.

The PCR reaction was performed in a reaction volume of 100 μL using 2 ng of pQZE533 DNA, primer concentrations of 0.4 ng/μL, 400 μM of each of the deoxynucleoside triphosphates, 2 mM $MgCl_2$, 0.5 units of Vent (exo⁻) DNA polymerase and 1×PCR reaction buffer (New England Biolabs) a Perkin-Elmer Cetus DNA thermal cycler machine was used for the reaction at an initial heat denaturation temperature of 95° C. for 5 min, then 30 cycles at a denaturation temperature of 95° C. for 1 min, an annealing temperature of 55° C. for 1 min and a polymerisation temperature of 72° C. for 1 min. A final polymerisation temperature of 72° C. for 7 min was used following completion of the 30 cycles. An aliquot (10 μL) from each of the completed PCR reactions was subjected to electrophoresis in a 1% agarose gel and the products visualised following ethidium bromide staining and UV transillumination. The PCR product of 790 bp was purified by phenol-chloroform extraction and ethanol precipitation. The purified PCR product was dissolved in LTE buffer (10 mM Trizma Base, 1 mM $Na_2EDTA$, pH8.0) and kept in −20° C. before use.

Purification of AlbD Enzyme.

Figure 10A:
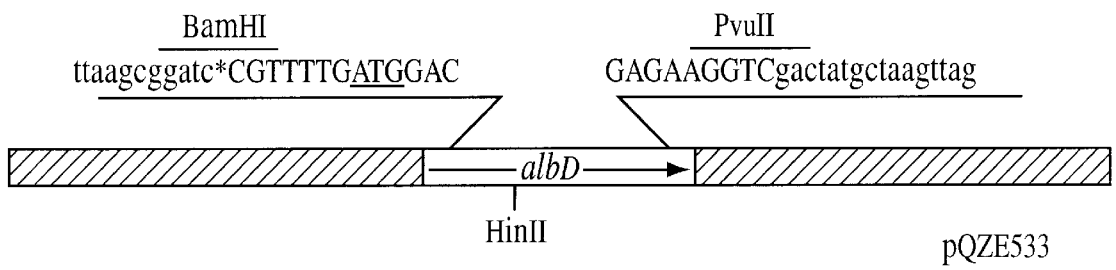
FIG. 10A (SEQ ID NO:7 and SEQ ID NO:8) is the same as FIG. 7A.
Figure 10B:
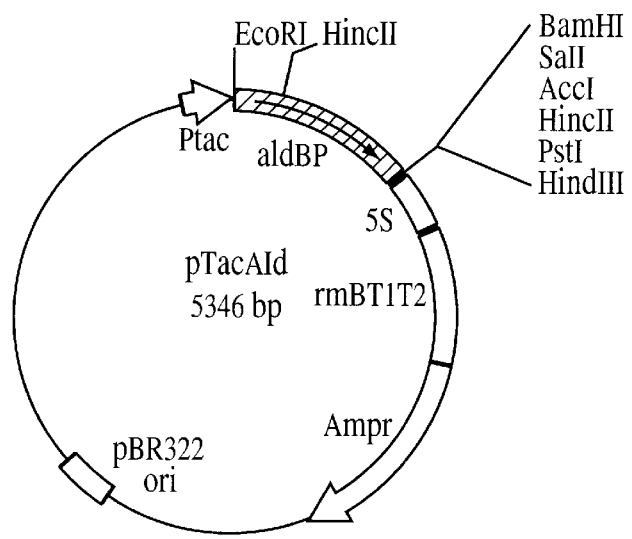
FIG. 10B refers to a map of a plasmid clone designated pTacAld showing the orientation of the albD structural gene portion under the influence of the tac promoter.

The PCR amplified structural gene fragment was digested by BamHI and PvuII and ligated to the BamHI and SmaI digested GST gene fusion vector pGEX-2T. The resultant construction pGSTAld contains the chimeric albD gene fused in frame to the glutathione S-transferase (GST) gene which is under the control of IPTG inducible tac promoter (FIG. 10).

E. coli DH5α (pGSTAld) was cultured and induced by IPTG. The purification of AlbD enzyme was basically following manufacturer's instruction (Pharmacia). Briefly, the bacterial culture was pelleted by centrifugation and cell free extracts were prepared by ultrasonification and applied to the Glutathione Sepharose 4B affinity column. The GST-AlbD fusion protein was bound to the affinity column matrix, and the AlbD enzyme protein was separated from the GST protein by digestion with protease Thrombin for 16 hours at room temperature. Following digestion, the eluate containing pure AlbD protein was collected and analysed by SDS-PAGE. The purified enzyme was kept in −20° C. in PBS buffer (140 mM NaCl, 2.7 mM KCl, 10 mM $Na_2HPO_4$, 1.8 mM $KH_2PO_4$, pH7.3) plus 20% glycerol.

Figure 11A:
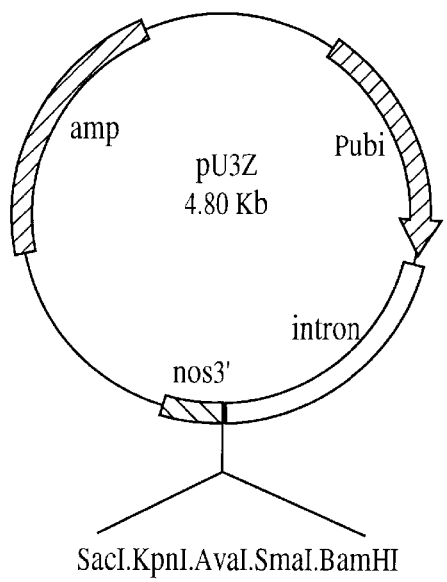
FIG. 11A illustrates a map of the sugarcane expression vector pU3Z.
Figure 11B:
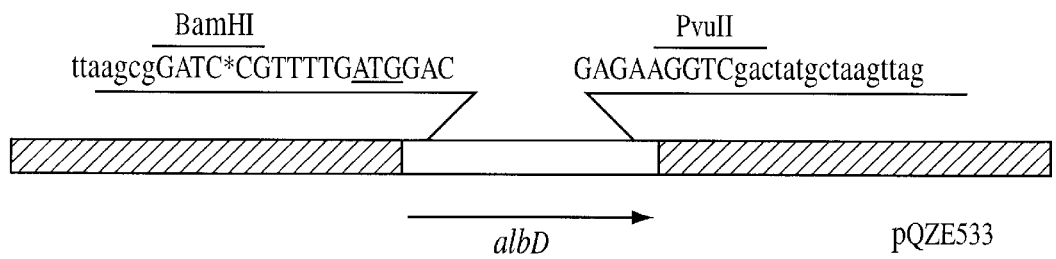
FIG. 11B (SEQ ID NO:7 and SEQ ID NO:8) is the same figure as FIG. 7A.
Figure 11C:
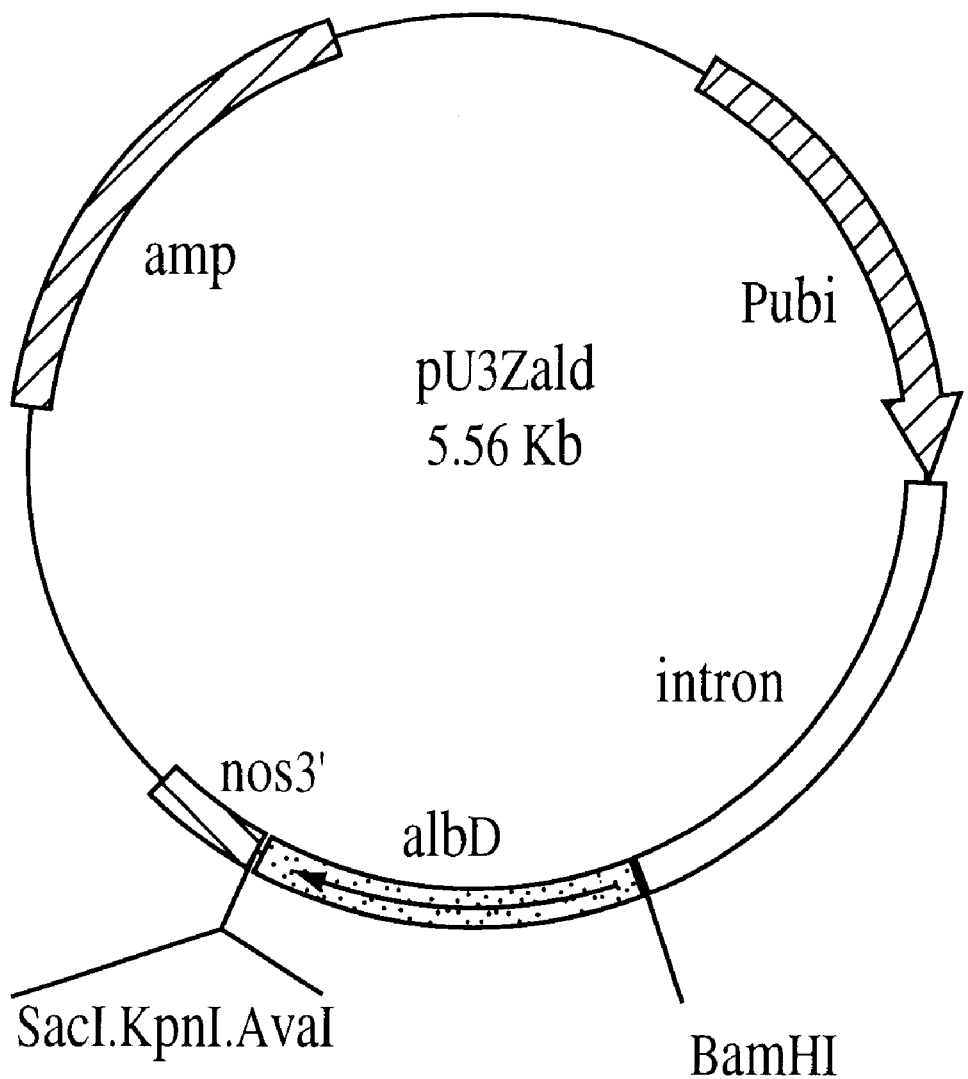
FIG. 11C. refers to a map of construct pU3ZALD.
Figure 12:
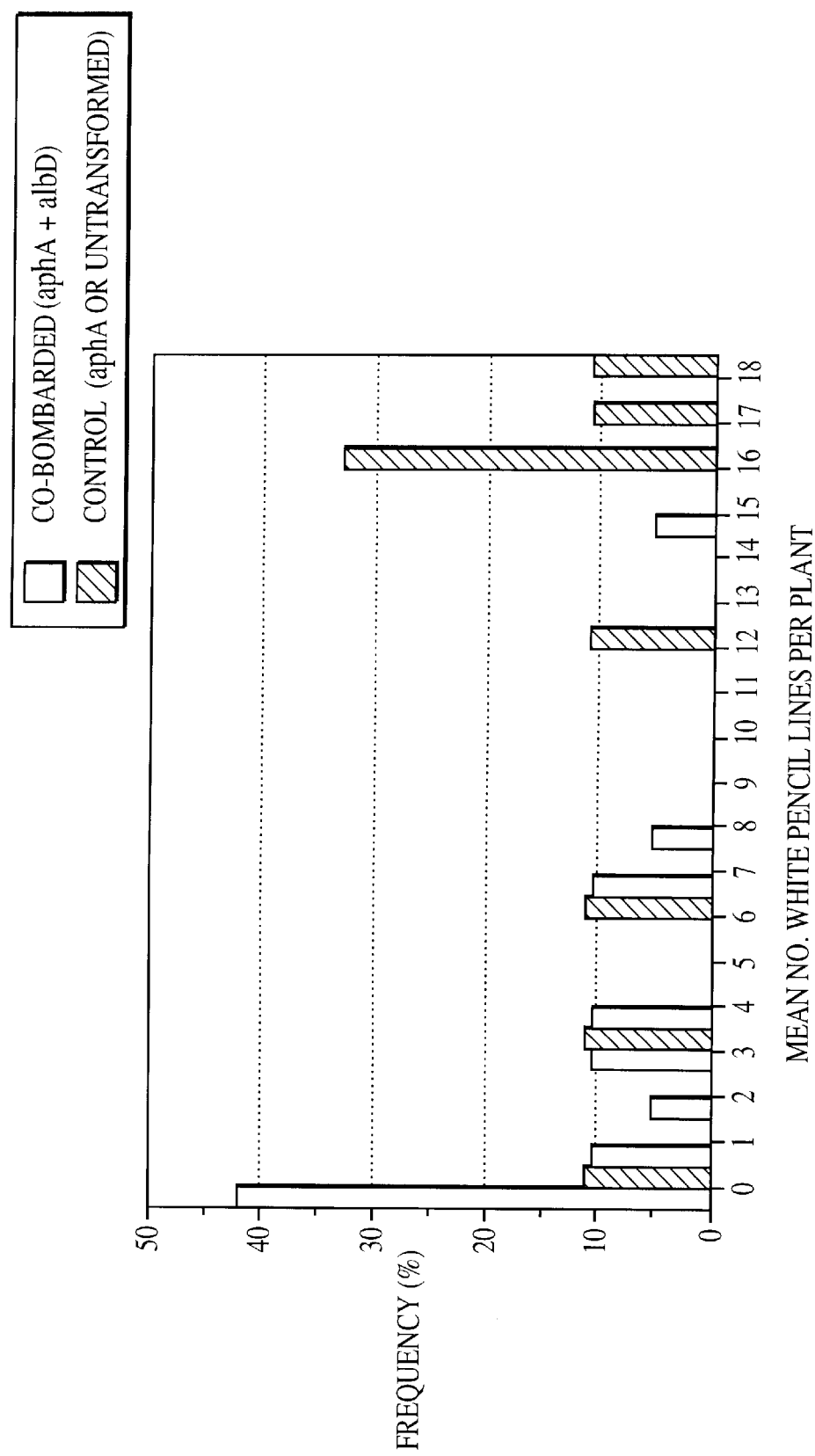
FIG. 12 refers to a bar graph showing the frequency distribution of disease severity in sugarcane cultivar Q63 plant lines regenerated from callus co-bombarded with albD wherein the plant lines were inoculated with *X. albilineans* XA3.

Monocot expression vector construction. The basis of the monocot expression vector constructs was pGEM-4Z. A 260 bp SstI-EcoRI fragment containing the terminator sequence (nos3') from the nopaline synthase gene of the Agrobacterium Ti plasmid was isolated from GUS gene fusion plasmid pBI101 (CLONTECH) and inserted into the SacI-EcoRI site of pGEM-4Z. The HindIII-BamHI fragment about 1.9 kb in size containing ubiquitin promoter and intron sequences was isolated from the construct pAHC18, which contains ubiquitin-promoter/luciferase (ubi-luc) fusion gene (Bruce et al., 1989. Proc. Natl. Acad. Sci. USA., 86, 9692–9696). This fragment was then ligated to the HindIII-BamHI sites of the pGEM-4Z::nos 3'. The resultant monocot expression vector pU3Z has several unique restriction enzyme sites such as BamHI, SmaI, KpnI and SacI in between promoter/intron and terminator region for subsequent cloning genes of interest (FIG. 11A).

pU3Zald and pU3ZGUS construction and transformation of sugarcane. To construct pU3Zald (FIG. 11C), the ubi-albD fusion gene, the PCR amplified BamHI-PvuII fragment of albD structural gene (FIG. 11B) was ligated to the pU3Z (FIG. 11A) linearized by BamHI and SmaI. The pU3ZGUS was constructed by fusion of the BamHI-SstI GUS fragment from pBI101 (CLONTECH) to the BamHI and SacI sites of vector pU3Z (map not shown). Transformation of sugarcane is briefly outlined as follows.

Embryogenic callus of the sugarcane cultivar Q63 was established and maintained as described by Franks and Birch, (1991), Aust. J. Plt. Physiol., 18, 471–480. The embryogenic callus was placed in a circle of 2.5 diameter on an osmoticum plate ($MSC_3$ plus 0.2M mannitol an 0.2M sorbitol) at 4 h prior to bombardment. The callus was bombarded with DNA-coated tungsten microprojectiles using the apparatus and techniques described by Franks and Birch (1991), Aust. J. Plt. Physiol., 18, 471–480. After bombardment the callus was kept on the same osmoticum plates for another 4 h before being transferred to MSC3 (Heinz and Mee, 1969) selective medium.

Selection procedures and regeneration of transgenic sugarcane. Following bombardment with constructs described under the sub-heading "Production and analysis of transgenic plants" as described hereinafter, embryogenic callus was cultured on an initial selection medium containing 20 μg/mL geneticin for 2 weeks. Healthy callus was transferred to medium containing 30 μg/mL geneticin for another 2 weeks. Escape-free selection was then applied by transferring the healthy callus to a $MSC_3$ medium containing 45 μg/mL geneticin for about 4 weeks. Then actively growing callus was transferred onto a regeneration MSC medium containing the same concentration of antibiotics. These regeneration plates were placed in the tissue culture room at 28° C. under fluorescent lighting. After about 2 weeks culture, small plantlets were separated and placed on the same regeneration medium for further growing until ready for establishment in pots.

Detection of AlbD enzyme expressed in transgenic sugarcane. One gram of sugarcane leaves were cut into small pieces and frozen in liquid nitrogen, ground into powder in a mortar before adding 4 ml of extraction buffer (100 mM $KPO_4$, 10 mM DTT, 1 mM EDTA, 3% Triton X-100, pH 7.0) buffer for further grinding for 1 min; transferred into a 10 mL tube and allowed to stand 30 mins in an ice box. Supernatants were collected after centrifugation at 4° C. for 20 min (14000 rpm). Protein concentrations in the supernatants were measured. Supernatants were added to albicidin solution and incubated for 2 h at 28° C. before bioassay. Disappearance of albicidin from the reaction mixture indicated the presence of AlbD enzyme.

RESULTS AND DISCUSSION

Isolation of Albicidin Resistant Bacteria

Fifteen different bacterial isolates that show differences in size, colour and shape of colonies on non-selective medium were collected from different parts of the X. albilineans infected sugarcane. Among them, thirteen isolates showed different levels of albicidin resistance, some are highly resistant (1000 u albicidin/mL), whereas others only show moderate or low levels of resistance (TABLE 2). In this investigation, one activity unit of albicidin was defined as the amount of toxin that could produce a 3 mm inhibition zone in the plate overlay bioassay (Birch and Patil, 1985, J. Gen. Microbiol., 131, 1069–1075).

Screening of Bacteria that can Produce Albicidin Detoxification Enzyme

Albicidin is heat stable and its activity is unaffected at 100° C. for 30 min (Walker et at., 1988, Molec. Microbiol., 2 (4), 443–454), whereas bacterial cell membrane and many proteins can be denatured by boiling for a short time. A simple and efficient assay was therefore designed to detect different albicidin resistant mechanisms. Bacterial isolates resistant to 500 u/mL albicidin were tested for their possible resistance mechanism. Some bacterial strains of known albicidin resistance mechanism were used as controls. The fresh bacterial cultures were mixed with albicidin solution, and the mixture was divided into two parts after incubation. One part was boiled, the other remain unboiled. Then the supernatants were assayed for albicidin. The results in TABLE 3 shows that albicidin activity was recovered by boiling the cells of *A. denitrificans* and *E. coli* (pBS6) which is the typical of reversible toxin binding mechanism (Basnayake and Birch, 1995, Microbiology, 141; Walker et al., 1988, Molec. Microbiol., 2 (4), 443–454). *E. coli* strain RR1 Alb$^r$, excludes albicidin from entering the bacterial cells. By comparison with these controls, we can classify those albicidin resistant isolates into three groups with different putative resistant mechanisms. Isolates SB1401 and SB1402 are likely to have a toxin reversible binding mechanism like *A. denitrificans* and *E. coli* (pBS6). The resistant mechanism of SB501, SB1301 and SB1404 could be toxin exclusion or resistant target. Isolates SB101, SB107 and SB1403 that were able to detoxify albicidin irreversibly are most likely to have albicidin detoxification enzymes. Among them, strain SB1403 shows the strongest albicidin detoxification activity.

Figure 1:
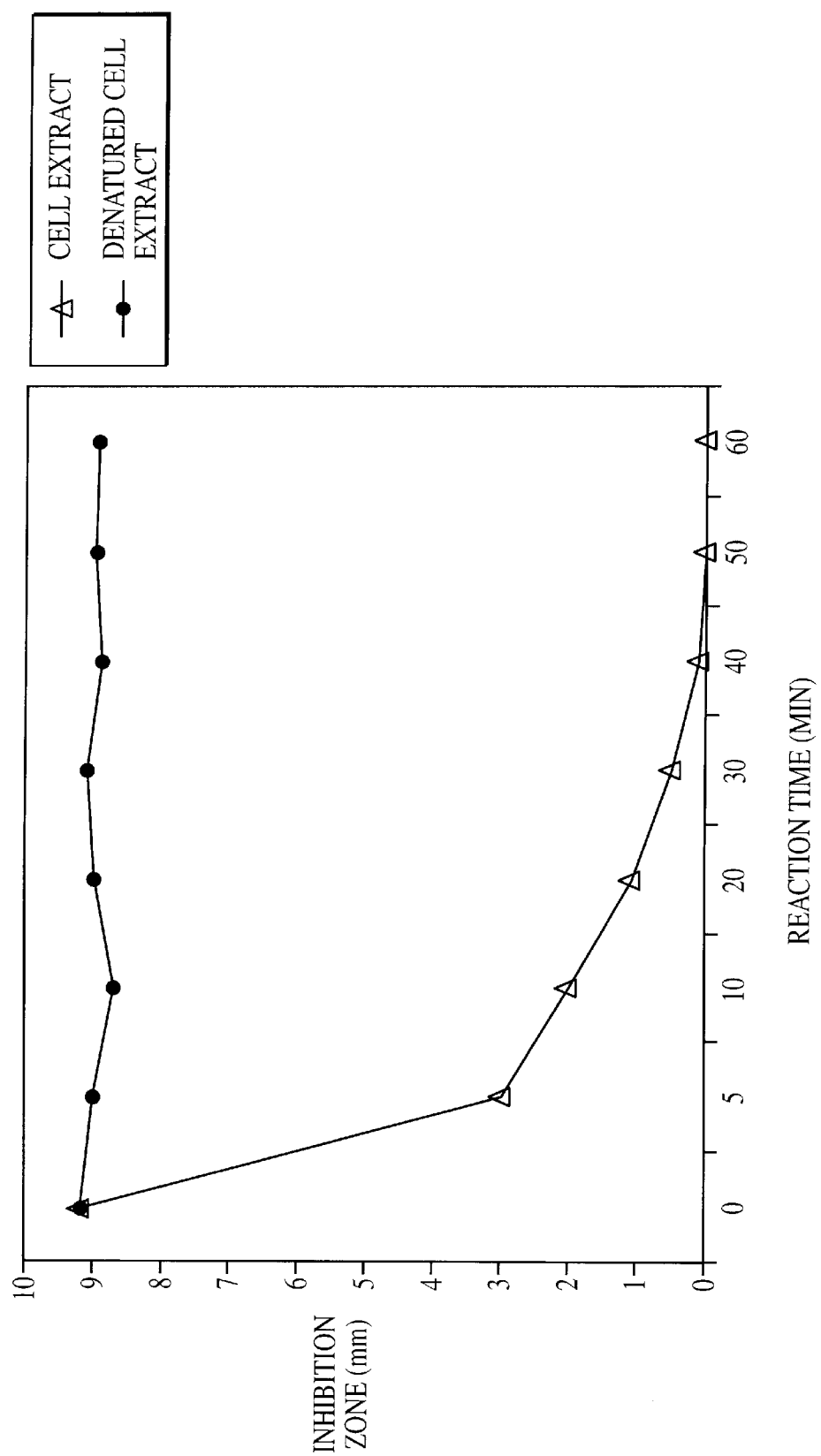
FIG. 1 refers to a time course of albicidin detoxification by cell free extracts of *E. herbicola* SB1403.

It is confirmed by the cell free extracts experiment that strain SB1403 can produce an albicidin detoxification enzyme. FIG. 1 is the time course reaction of cell free extracts of SB1403. In the presence of active cell free extracts, albicidin has been rapidly and progressively removed from the reaction mixture. But almost all toxin added remained in the reaction mixture if the cell free extracts were denatured by boiling before reacting with albicidin.

Identification of Strain SB1403

Strain SB1403 is gram-negative, ONPG test positive, motile and rod-shaped bacterium with 4–8 peritrichous flagella. Its cell size was about 0.6–1.0 μm wide×1.3–3.0 μm long. It can produce yellow pigment on SP medium. A positive reaction resulted in the test for oxidation or fermentation of glucose in Hugh and Leifson's medium. The strain was further classified by using GN MicroPlates which contain 95 carbon source utilisation tests (BIOLOG). In this assay, utilisation of a carbon is detected as an increase in the respiration of cells in the well, leading to irreversible reduction of tetrazolium dye. The "breathprint" thus obtained was matched to the Gram-negative Database containing identification patterns of 569 Gram-negative species/groups. The matching results show that the isolate SB1403 was *Erwina herbicola* (*Enterobacter agglomerans* A).

Biocontrol of Leaf Scald by *E. herbicola* SB1403

TABLE 4 shows that *E. herbicola* SB1403 was very effective in the biocontrol of leaf scald disease. *X. albilineans* caused a severe damage to sugarcane Q44, 50% of the newly emerged leaves after inoculation were dead, and there were 139 white pencil lines observed in surviving leaves. But in those plants co-inoculated with *E. herbicola* SB1403, none of the leaves was dead and only 2 or 3 white pencil lines were observed. Furthermore, biocontrol agent *E. herbicola* did not have any detectable side effect on sugarcane.

Some antibiotic producing *E. herbicola* isolates are used in biocontrol of fire blight, a disease of rosaceous plants caused by *Erwinia amylovora* (Vanneste et al., 1992, Journal of Bacteriology, 174, 2785–2796). But *E. herbicola* SB1403 did not produce any detectable antibiotic against *E. coli* and *X. albilineans*. Determination of the role of albicidin detoxification enzyme production by *E. herbicola* SB1403 in the biocontrol of leaf scald disease will be described in a later section.

Cloning Albicidin Detoxification Gene

Figure 2:
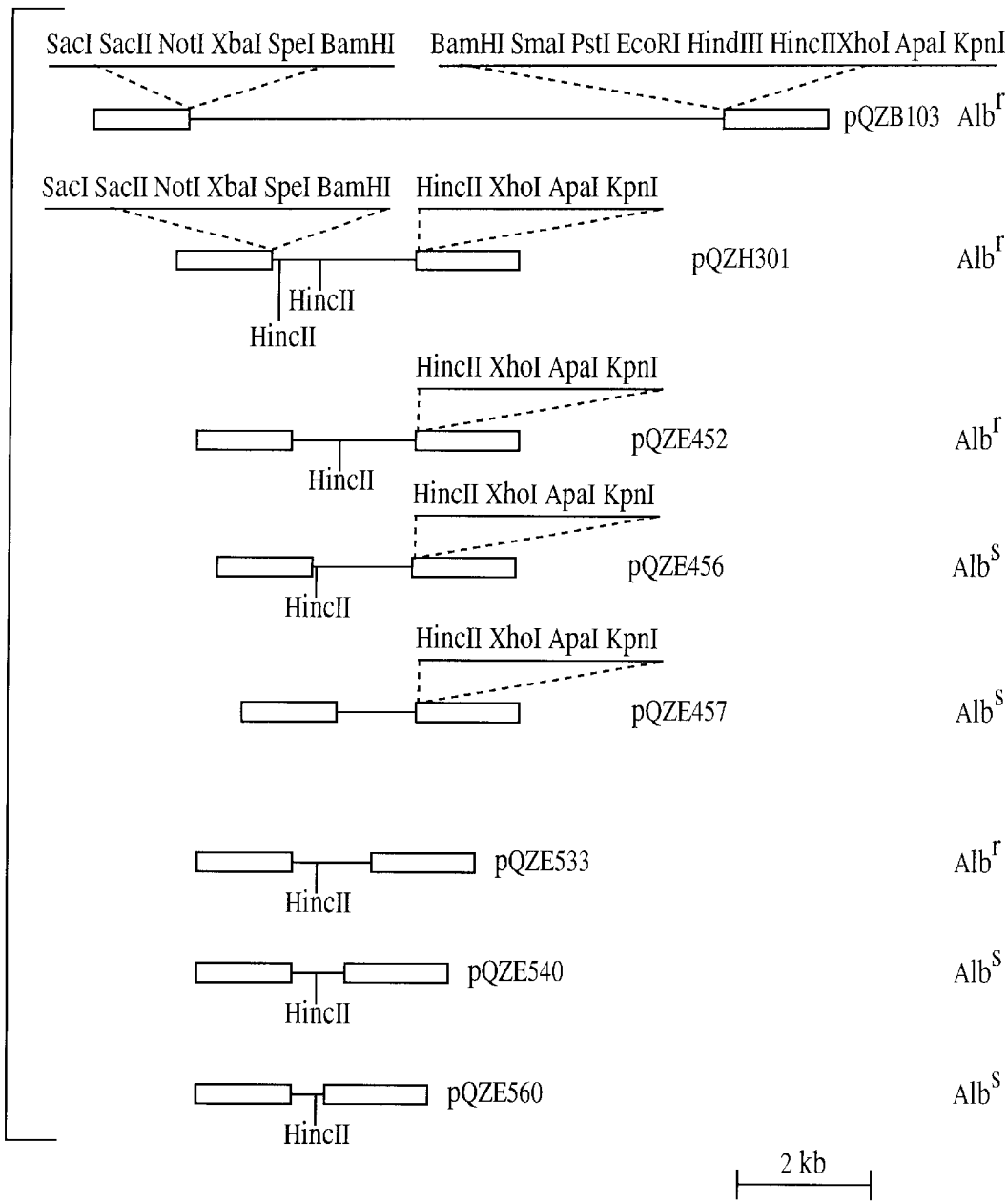
FIG. 2 illustrates a physical map of QZB103 and derivatives thereof.

About 1600 Tc$^r$ cosmid clones were patched on to LB plates containing 500 u/mL albicidin, and 5 albicidin resistant strains were detected. The cosmids from 4 strains were digested with BamHl and all found to contain a 8 kb common band. This common fragment was cloned into the DNA sequencing vector pBluescript and named pQZB103 (FIG. 2). The plasmid DNA of pQZB103 was partially digested by HincII and religated. The religation products were used to transform *E. coli* DH5α and transformants were selected on LB plates containing albicidin. The plasmids of albicidin resistant colonies were isolated and their sizes were determined by agarose gel electrophoresis. Restriction enzyme digestion of the smallest plasmid clone pQZH301 showed that it contained only two HincII fragments, one is 1.9 kb in size and the other is 0.6 kb. A range of subclones of pQZB301 were obtained by double exonuclease III unidirectional deletions and religation to the cloning vector. Each of these plasmids was transformed into *E. coli* DH5α and sensitivity of each to albicidin was determined (FIG. 2). All of the Alb$^r$ clones remained sensitive to bacteriophage T6 infection, indicating resistance is not due to the spontaneous mutation of the Tsx pore involved in albicidin uptake (Birch et al., 1990, J. Gen. Microbiol, 136, 51–58).

Nucleotide Sequence of the Albicidin Detoxification Gene

The DNA sequence and the inferred amino acid sequence of a portion of this albD gene is shown on FIGS. 3A and FIGS. 3B–3F. We find only one open reading frame reading, which could encode a hydrophilic protein of 235 amino acids, having a molecular weight of 24511 daltons. Of the 235 amino acids in the AlbD protein, there are 59 charged residues; 32 are acidic and 27 are basic, resulting an isoelectric point at 6.23. The best complementary sequence to the 16s rRNA 3'-UCUUUCCUCCACUA sequence (SEQ ID NO:11) was found 10 bp upstream from the ATG initiation codon leading the only open reading frame (shadowed), but it does not match well to the AGGAGG Shine-Dalgarno sequence (Shine and Dalgarno, 1974, Proc. Natl. Acad. Sci. USA., 71, 1342–1346).

The transcription termination site of albD possibly belongs to the factor-independent group (Platt, 1986, Annu. Rev. Biochem., 55, 339–372). Two TCTT boxes and a TGTG box that are closely resemble the TCTG consensus sequence characteristic of factor-independent termination sites (Brendel and Trifonov, 1984, Nucleic Acids Research, 12, 4411–4427) were found downstream of the termination codon of albD gene. Besides, T-rich regions are located upstream of the two TCTT boxes although T-content is not highly significant. But there is no GC-rich dyad symmetry region downstream the termination codon.

The FASTA program of Lipman and Pearson was used to compare the DNA (FIGS. 3B–3F) (SEQ ID NO:2) and protein sequences (FIG. 3A) (SEQ ID NO:1) of this gene to all DNA and Protein sequences in major sequence databases (GenBank, EMBL, PIR and Swiss-Prot) through the Australian National Genomic information Service. However, no significant similarity has been detected to any known DNA or protein sequences. In this regard, the prior art sequences exhibiting the greatest homology at the protein level comprised mouse T-cell-specific transcription factor –1P (28.7% identity in a 136 aa overlap, PIR Accession #JH0401);

*Agrobacterium tumefaciens* hypothetical protein 2 (29.0% identity in a 107 aa overlap, PIR Accession #S07977); *Bacillus subtilis* dihydroorotase (30.5% identity in a 95 aa overlap, PIR Accession #D39845); *Rhizobium meliloti* flagellin flaA (21.4% identity in a 154 aa overlap, PIR Accession #A39436); *Pseudomonas cepacia* beta-lactamase (22.4% identity in a 210 aa overlap, PIR Accession #A48903); and *Xanthomonas campestris* copD homolog (28.3% identity in a 152 aa overlap, PIR Accession #D36868).

We also compared the AlbD protein sequence with the conserved region of the two known albicidin binding proteins (Walker et al., 1988, Molec. Microbiol., 2 (4), 443–454; Basnayake and Birch, 1995, Microbiology, 141). FIG. 4 shows the best match of the AlbD amino sequence to the first 16 amino acids at the N terminus of the Alb$^r$ binding proteins from *K. oxytoca* and *A. denitrificans* respectively. This short oligopeptide is the only significantly conserved region in the two proteins and is likely to be the albicidin binding domain (Basnayake and Birch, 1995, Microbiology, 141). As shown in FIG. 4, the motif for these three albicidin resistant proteins seems to be "SxxxLxxL" or less strictly "MYxxxFSxxxLxxLxL" (SEQ ID NO:12).

The Role of AlbD Enzyme of *E. herbicola* SB1403 in Biocontrol of *X. albilineans*

*E. herbicola* SB1403 provided a very effective biocontrol of leaf scald disease caused by *X. albilineans* (TABLE 4). To establish the role of albicidin detoxification enzyme produced by SB1403 in the control of leaf scald, we isolated site-directed mutants of SB1403 that lost the ability to produce AlbD enzyme, and compared their effectiveness in the biocontrol of leaf scald to that of their parent strain.

Figure 5A:
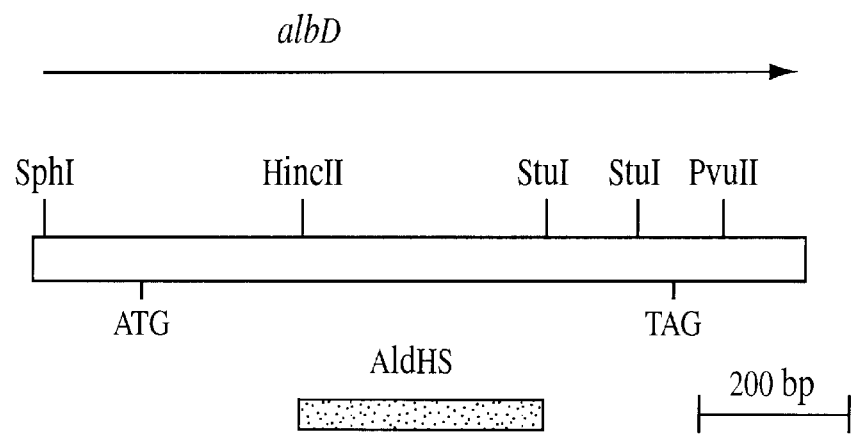
FIG. 5A illustrates the internal HincII-StuI fragment of the albD gene.
Figure 5B:
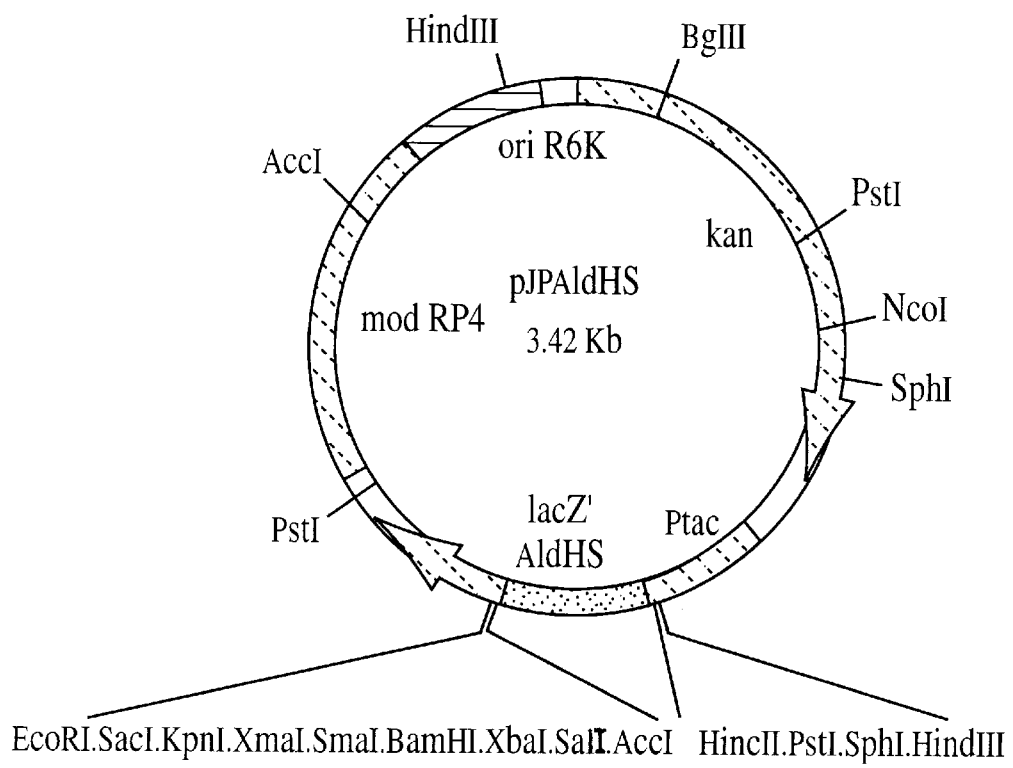
FIG. 5B refers to a map of plasmid pJPAldHS.

A "universal" suicide vector pJP5603 that replicates only if the R6K pir gene is supplied in trans was used for generation of albD gene insertion mutation in SB1403 (Penfold and Pemberton, 1992, Gene, 118, 145–146). A HincII-StuI internal fragment of AlbD gene was cloned into pJP5603, the resultant recombinant clone pJPAldHS (FIG. 5) was mobilised into SB1403. Transconjugant colonies were obtained at a frequency of 3.5×10$^{-7}$, and 75% of colonies lost their ability to produce AlbD enzyme, indicating that albD has been successfully mutated. This also shows that the albD gene is not essential for bacterial growth and that it is a single copy gene.

Two AlbD$^-$ mutants of SB1403 have been tested in biocontrol of leaf scald disease. TABLE 5 shows that sugarcane co-inoculated with *X. albilineans* XA3 and *E. herbicola* SM1 or SM18 had about 5 times more white pencil lines compared to those plants treated with XA3 and SB1403rif. These data indicate that AlbD enzyme is contributing to biocontrol of leaf scald.

Comparison of the Activities of Cloned albB and albD Gene Products in *E. coli*

Figure 6:
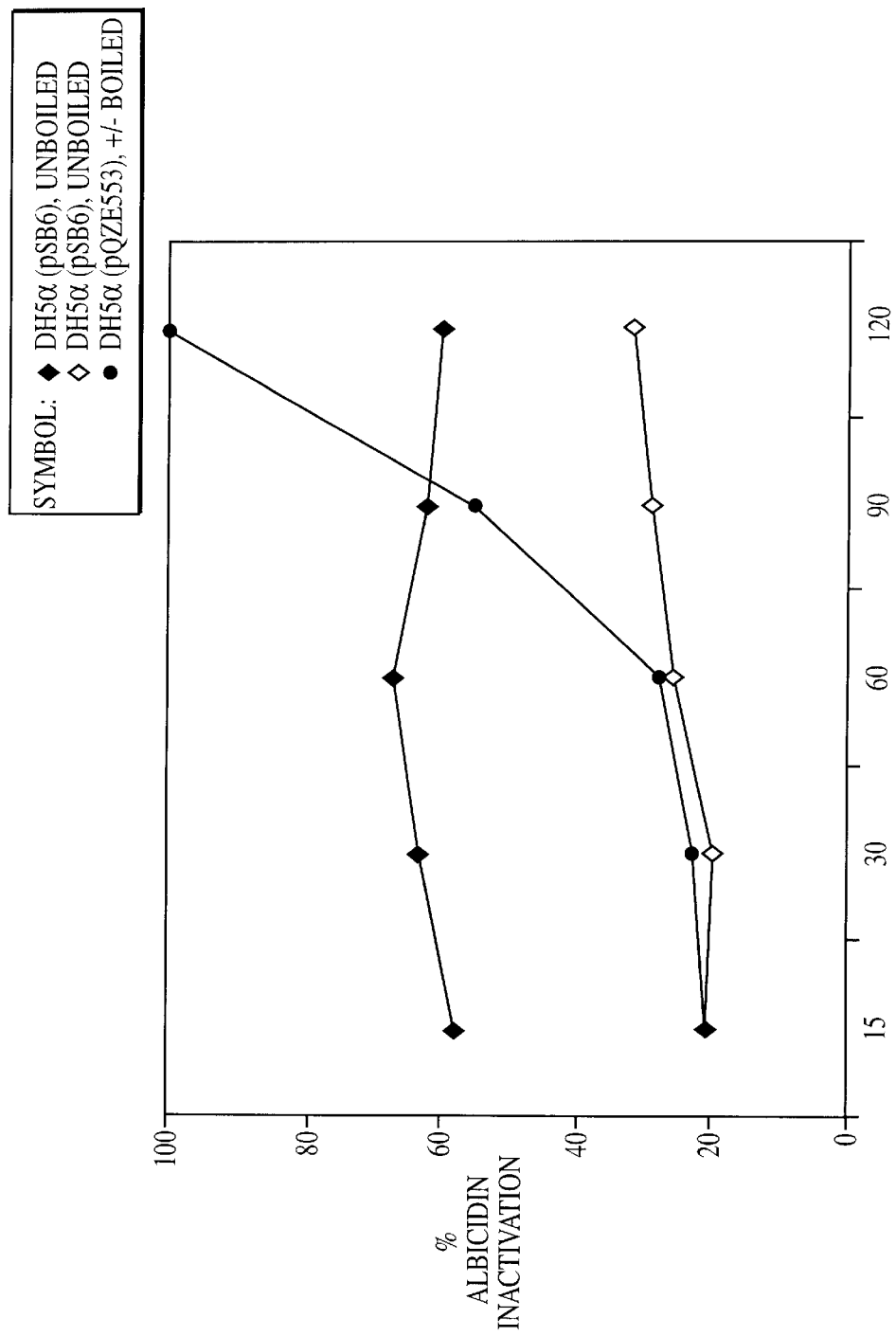
FIG. 6 refers to a graph showing inactivation of albicidin by *E. coli* DH5α [pQZE533] and *E. coli* DH5α [pSB6]

FIG. 6 shows the relative albicidin inactivation activities of *E.coli* DH5α [pSB6] containing albB cloned from *A. denitrificans* and *E. coli* DH5α [pQZE533] containing albD gene cloned from *E. herbicola* SB1403. DH5α [pQZE533] gradually removed albicidin from the reaction mixture and gave 100% irreversible detoxification of albicidin within 120 min. Strain DH5α [pSB6] reduced anti-microbial activity by more than 50% within the first 15 min, but there was no further reduction. This is possible because binding proteins bind and thus inactivates albicidin in a molar ratio of 1 binding protein: 1 albicidin (Basnayake and Birch, 1995, Microbiology, 141). Protein bound albicidin is inactive in the anti-microbial assay. Once the binding protein pool was exhausted by forming unrecyclable protein:albicidin complexes, DNA synthesis in the bacteria cell could be inhibited by excessive albicidin. Reduced anti-microbial activity of albicidin by binding protein is reversible; a large proportion of toxin activity was released when the protein-:albicidin complex was denatured by boiling. The data indicate that AlbD enzyme results in irreversible detoxification of albicidin than AlbB binding protein, a much more effective method of albicidin resistance than reversible interaction with albicidin binding protein.

Purification and Properties of AlbD Enzyme

GST gene fusion system (Smith and Johnson, 1988. Gene 67: 31–40) was used to purify the albicidin detoxification enzymes, the product of albD gene. The PCR amplified albD structural gene portion was fused to the C. terminus of glutathione S-transferase (GST) gene in the same open reading frame (FIG. 7). The fusion protein expressed in *E. coli* DH5α after induction by IPTG was bound to the GST affinity column. The pure AlbD enzyme protein was released from the column after digestion of the fusion protein with site specific protease Thrombin which recognises the cleavage-recognition sequences at the recombinant C terminus of the GST. SDS/PAGE analysis showed that the purified AlbD enzyme has a molecular masses of about 25.5 kDa, this is consistent with the predicated 25411 kDa molecular masses of the AlbD protein.

Figure 8:
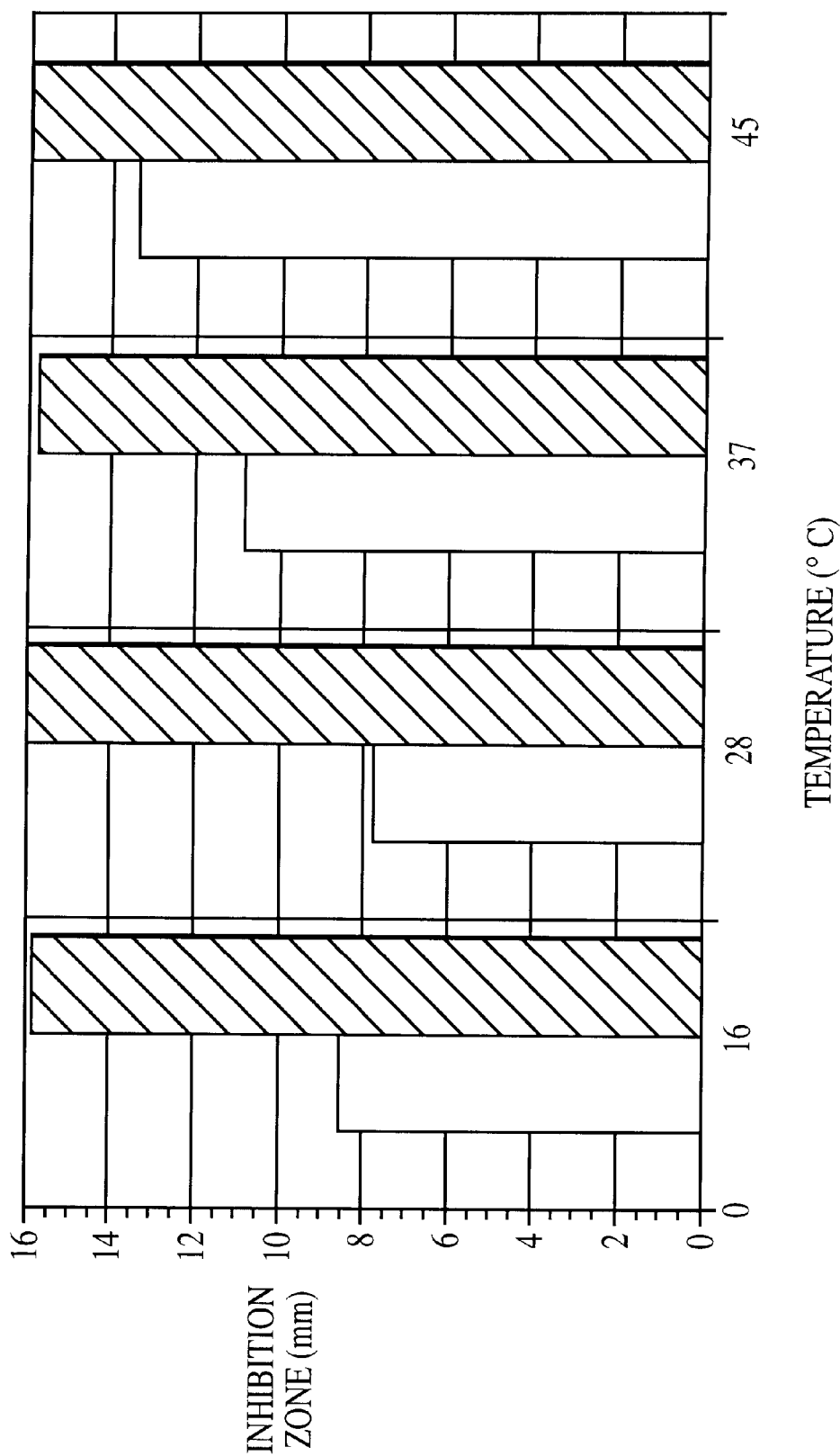
FIG. 8 shows a bar graph of the effect of temperature on AlbD enzyme activity.
Figure 9:
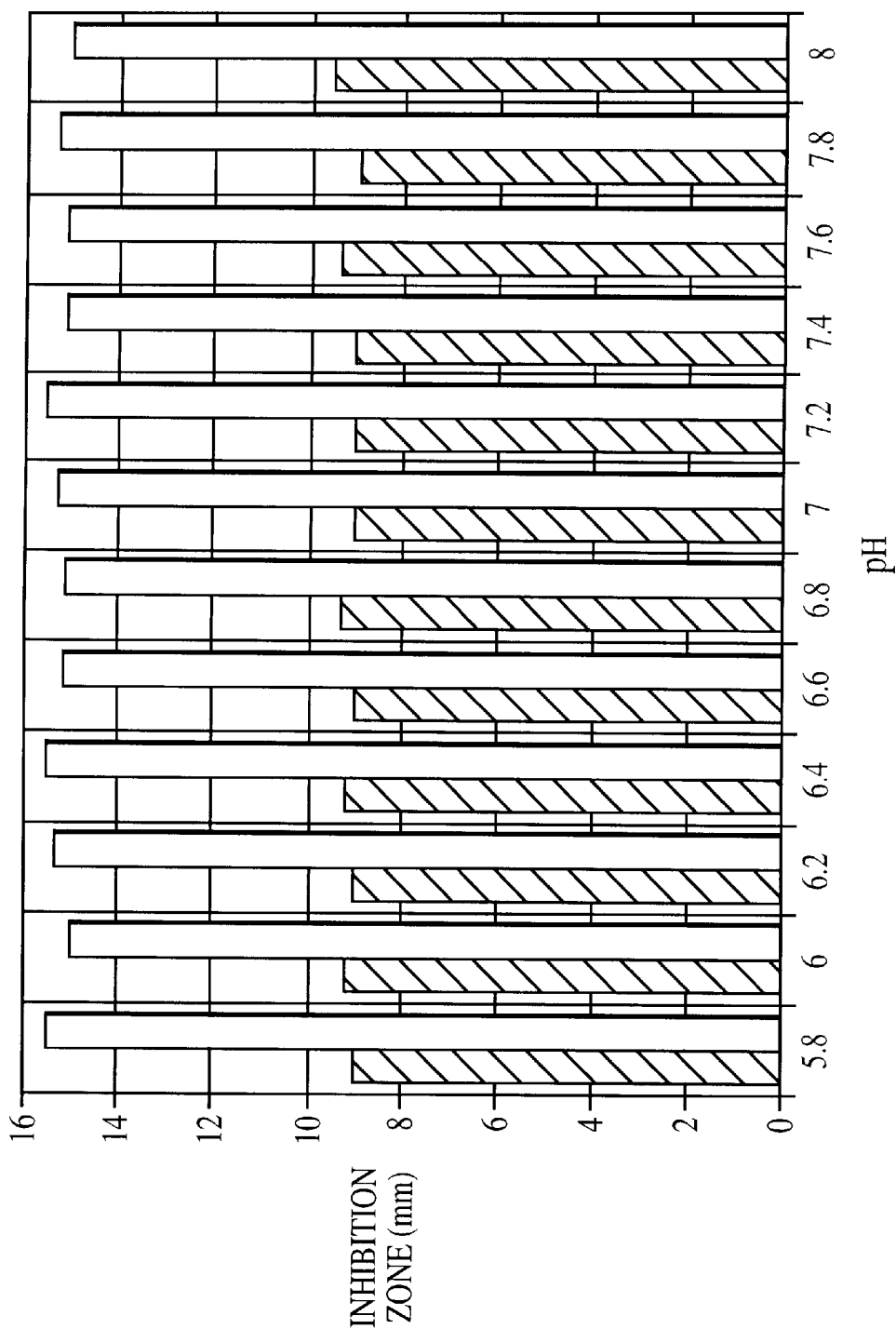
FIG. 9 represents a bar graph illustrating the effect of pH on AlbD enzyme activity.

The purified AlbD enzyme can be stably maintained in 20% glycerol buffer at −20° C. FIG. 8 shows that the enzyme can detoxify albicidin at 45° C., but prefers mild temperatures with the maximum activity at 28° C. FIG. 9 shows that the AlbD enzyme was not sensitive to changes of pH in the reaction solutions; the enzyme detoxified albicidin almost equally well in a range from pH 5.8 to pH 8.0.

As purified enzyme can effectively detoxify relatively pure albicidin in a very simple phosphate buffer, it seems that the AlbD enzyme does not require any complex cofactor for its activity.

These properties of AlbD enzyme suggest that it would work efficiently in the cytoplasm or plastids of plant cells.

DNA modification for Expression in Plant

In the native albD gene, there is an out of frame ATG initiation codon 8 bp upstream of +1 bp which could interfere with the high level expression of the albD gene when transferred into plants. This spurious start codon was eliminated by incorporating a point mutation in the PCR forward primer of the albD gene. As a result, the ATG has been changed to ATC, and this change also creates a restriction enzyme BamHI site on the 5' end of the albD gene PCR product which was used in the subsequent cloning (FIG. 10).

The PCR amplified promoterless albD structural gene portion was fused to the tac promoter of the bacterial expression vector pKK223-3 (Pharmacia). One of the resultant clones, pTacAld was identified containing correctly oriented tac-albD fusion gene (FIG. 10). The correct function was confirmed by demonstration of albicidin detoxification by pTacAld transformed *E. coli* (data not shown).

Production and Analysis of Transgenic Plants

To test whether this novel albicidin detoxification gene can also confer resistance to leaf scald disease in sugarcane, the PCR amplified promoterless albD structural gene portion was inserted in between the ubi-intron promoter region and the nopaline synthase polyadenylation signal on the monocot expression vector pU3Z (FIG. 11). The resulting plasmid pU3ZAld was used for transformation of the chimeric albD gene into sugarcane (Q63) by microprojectile bombardment (Bower and Birch, 1992, Plant J., 2, 409–416). The neomycin phosphotransferase (npt-II) gene encoding resistance to geneticin under the control of the synthetic Emu monocot promoter (pEmuKN) was co-transferred with pU3Zald into sugarcane to provide a selectable marker. As a control, the ubi-luc and ubi-gus reporter gene constructs pAHC18 and pU3ZGUS was co-transferred in the same way with pEmuKN into sugarcane. The stable transformed embryogenic callus was selected on medium containing geneticin and regenerated.

Crude protein extracts from leaves of a selection of Q63 plants including untransformed controls, lines transformed with the gus reporter system, and lines selcted after co-bombardment with albD were tested for capacity to inactivate albicidin. TABLE 6 shows that no albicidin detoxification was detected in negative control lines. However, activity was detected in various transformed lines, indicating that the albD gene had been stably integrated and expressed in these transgenic lines. Furthermore, the transgenic lines with albicidin detoxification activity as a result of expression of albD were resistant to leaf scald disease as indicated by absence of characteristic white pencil lines on inoculated leaves (TABLE 6). Not all lines co-bombarded with albD showed albicidin detoxification activity or disease resistance. This is the expected result because transgenic lines were selected only for antibiotic G418 (geneticin) resistance, a phenotype encoded by the aphA (nptl) gene. The efficiency of co-expression of other genes co-bombarded with aphA under these condition is typically in the range of 20% to 60%.

Challenging the Trangenic Plants with the Pathogen

After growth in the greenhouse for about 3 months, plants were challenged with *X. albilineans* strain XA3 or XA15. FIGS. 12–13 show that many transgenic plants regenerated after co-bombardment with albD showed increased resistance to leaf scald disease, as indicated by few or no characteristic white pencil line symptoms on inoculated leaves, whereas control lines not bombarded with albD typically developed multiple white pencil lines. Absence of white pencil lines in transgenic lines was associated with capacity for detoxification of albicidin (TABLE 6).

CONCLUSION

A bacterial strain SB1403 producing a strong phytotoxin (albicidin) detoxification enzyme (AlbD enzyme) has been isolated and identified as *Erwinia herbicola* (or *Pantoea dispersa*). SB1403 was very effective in the biocontrol of sugarcane leaf scald disease caused by *X. albilineans*, and AlbD enzyme is one of the determinants of the biocontrol.

The gene encoding AlbD enzyme has been cloned and sequenced. The albD gene is a novel gene, there is not any significant sequence homology at either DNA or protein levels to any other known DNA or protein sequences.

The AlbD enzyme has been purified to homogeneity. The enzyme inactivates albicidin effectively at pH ranging from 5.8–8.0. The optimum temperature for the enzyme activity is 28° C. The enzyme has no complex cofactor requirement.

An out of frame ATG (start) codon which would interfere with expression in plant cells was removed by PCR. The PCR modified coding sequence of albD gene was cloned into a sugarcane expression vector including the maize ubiquitin promoter and nopaline synthase 3' terminator. It has been introduced into sugarcane by particle bombardment. The transgenic plants expressing AlbD enzyme were resistant to leaf scald disease caused by *X. albilineans*.

EXAMPLE 2

Biocontrol of Leaf Scald Disease in Sugarcane by a Strain of *Pantoea dispersa* which Inactivates Albicidin

MATERIALS AND METHODS

Bacteria, media and growth conditions. *X. albilineans* strain XA3 was isolated from leaf scald diseased sugarcane as described previously (Birch and Patil, 1987, Physiological and Molecular Plant Pathology, 30, 199–206). All other bacteria used in the study are listed in Table 7. *Escherichia coli* was grown in LM medium (Miller, 1972, Experiments in Molecular Genetics, Cold Spring Harbour, N.Y.: Cold Spring Harbour Laboratory Press) at 37° C. All other bacteria were grown in SP medium (Birch and Patil, 1985, J. Gen. Microbiol., 131, 1069–1075) at 28° C. Broth cultures were aerated by shaking at 180 rpm on an orbital shaker.

Preparation and assay of albicidin. Albicidins produced in culture by *X. albilineans* strain XA3 were purified as described previously (Birch and Patil, 1985, J. Gen. Microbiol., 131, 1069–1075; Birch et al., 1990, J. Gen. Microbiol., 136, 51–58). The mixture of albicidins obtained after HW-40(S) chromatography was used in experiments reported here. Albicidin was quantified as described previously (Birch and Patil, 1985, J. Gen. Microbiol., 131, 1069–1075), except that *E. coli* strain DH5 was used as the indicator strain, and 1% agarose was used for overlayers.

Isolation of albicidin resistant bacteria. Leaf scald diseased sugarcane was collected from disease resistance trials conducted by the Bureau of Sugar Experiment Stations in Brisbane, Australia. Leaf and stem samples showing symptoms of invasion by *X. albilineans* were surface sterilised by 70% ethanol, then finely chopped, and suspended in sterilised water with shaking for 1 h before spreading over SP agar plates. Visibly distinct colony types were restreaked to ensure purity of isolates, which were tested for albicidin resistance by streaking onto plates containing specified concentrations of the antibiotic.

Test of albicidin resistance mechanism. Actively growing bacterial culture (optical density at 600 nm of 1.5) was added to an equal volume of SP broth containing albicidin at a final concentration of 500 ng $ml^{-1}$, then incubated at 28° C. for 6 h. Samples were placed on ice or boiled for 5 min, then centrifuged at 11020×g for 10 min. Supernatants were assayed for albicidin, after exposure to UV (312 nm) for 10 min to kill cells in unboiled treatments.

Albicidin inactivation by cell free filtrates and cell extracts. Strain SB1403 was grown in broth for 40 h then chilled in ice and centrifuged at 11020×g for 10 min. The supernatant was filter sterilized (Gelman Acrodisc® 0.2 μm), then stored on ice or treated with 20 μg $ml^{-1}$ protease K (signma) for 1 h at 28° C. Capacity to inactive albicidin in SP broth was then tested as described above.

To prepare cell extracts, cells from a 24 h broth culture were harvested by centrifugation at 11020×g for 10 min, washed and resuspended in TEMM buffer (10 mmol $1^{-1}$ Tris pH 7.45, 10 mmol $1^{-1}$ EDTA, 10 MMOL $1^{-1}$ $MgCl_2$ and 2 mmol $1^{-1}$ β-mercaptoethanol), and disrupted by sonification on ice with a microprobe (Branson model 250), at 50% duty cycle and an output of 25–45 W for 3 min of 8 s sonification followed by 8 s rest periods. Cell disruption was confirmed by phase contrast microscopy. Cell debris was removed by centrifugation at 11020×g for 20 min at 4° C. Protein concentrations in cell extracts were measured by dye-binding (Bradford, 1976, Analytical Biochemistry, 72, 248–254), using bovine serum albumin for calibration.

Taxonomic identification and antibiosis assays. Strain SB1403 was tested for oxidation and fermentation of glucose using the Hugh and Leifson test (Collins and Lyne, 1984, Microbiological Methods, 5th edn., London: Butterworths), production of β-galactosidase (ONPG test), utilisation of carbon sources in the BIOLOG GN Microplate system (Biolog Inc.), and solubility in 3% KOH as a predication of the Gram reaction (Suslow et al., 1982, Phytopathology, 72, 917–918).

Antibiotic production by strain SB1403 was tested using *E. coli* DH5a and *X. albilineans* XA3 as indicator strains. Cell free culture filtrates after 1, 2 and 3 d growth in SP broth were tested using overlayer assays as described for albicidin. Colonies after incubation for 2 d on SP agar were killed by exposure to $CHCl_3$ vapour, then overlaid with the indicator bacteria.

Plant material and bacterial inoculation. Sugarcane variety Q44 which is highly susceptible to leaf scald disease was used in all biocontrol experiments. Single-node cuttings from healthy plants were grown in a greenhouse for about two months before inoculation with *X. albilineans* and *P. dispersa* strains by a decapitation method as described previously (Birch and Patil, 1983, Phytopathology, 73, 1368–1374). The inoculum consisted of bacteria from actively growing cultures (2 d culture of *X. albilineans* and 24 h culture of *P. dispersa*), which were centrifuged for 1 min at 11020×g, resuspended and diluted with sterilised water to specified concentrations, and kept on ice until inoculation. The inoculum was applied by coating onto the freshly cut surface of the plant.

Plants were inspected 2 weeks after inoculation for symptoms on cut leaves, and systemic symptom development was monitored for 6 months. Resolution of bacteria was attempted from inoculated leaves after 1 month, and from young stem tissue 6 months after inoculation. SP plates containing 200 $\mu$g ml$^{-1}$ ampicillin or 500 ng ml$^{-1}$ ampicillin or 500 ng ml$^{-1}$ albicidin were used to selectively reisolate *X. albilineans* ZA3 and *P. dispersa* SB1403 respectively.

RESULTS AND DISCUSSION

Isolation of albicidin resistant bacteria. Of fifteen bacteria with distinct colony characteristics isolated from *X. albilineans* infected sugarcane, thirteen isolates proved resistant to albicidin at 50 ng ml$^{-1}$ (the minimum inhibitory concentration for *E. coli*). Three isolates were resistant to 1000 ng ml$^{-1}$ albicidin (TABLE 1).

Screening for bacteria that detoxify albicidin. Many bacteria actively accumulate albicidin from the surrounding medium. In the case of *E. coli* this process is known to involve active uptake via the Tsx outer membrane pore, and diminished uptake results in albicidin resistance (Birch et al., 1990, J. Gen. Microbiol., 136, 51–58). Some bacteria are resistant to albicidin due to production of an intracellular protein which binds the antibiotic (Walker et al., 1988, Molecular Microbiology, 2, 443–454; Basnayake and Birch, 1995, Microbiology, 141, 551–560). Albicidin is heat stable and little activity is lost at 100° C. for 30 min, whereas bacterial cell membranes and many proteins are denatured by boiling, releasing reversibly bound albicidin. This allows a simple assay to distinguish various mechanisms of albicidin resistance. Bacterial samples are mixed with albicidin solution, aliquots are removed after incubation and kept on ice or boiled before assaying for albicidin activity in the supernatants. When fresh bacterial cultures are used, the assay distinguishes toxin inactivation from other known resistance mechanisms. Use of dense cell suspensions, cell extracts or culture supernatants in the assay further distinguishes toxin exclusion, toxin binding, probable resistant target, and intracellular versus exported proteins as resistance mechanisms.

Figure 13:
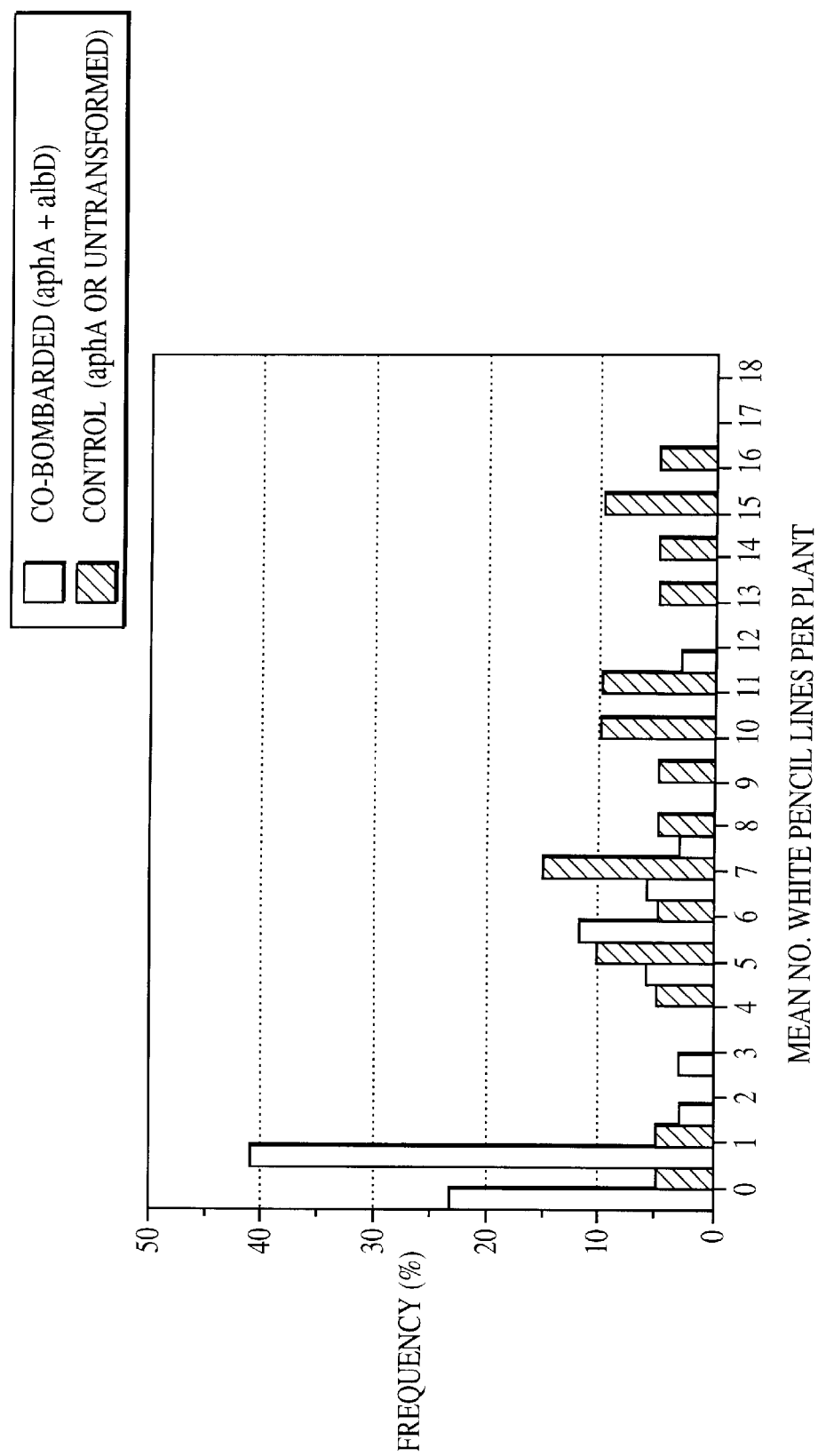
FIG. 13 illustrates a bar graph showing the frequency distribution of disease severity in sugarcane cultivar Q63 plant lines regenerated from callus co-bombarded with albD wherein the plant lines were inoculated with *X. albilineans* XA15.

Results using fresh cultures of the albicidin resistant bacteria from sugarcane, compared to controls with known resistance mechanisms, indicate diverse resistance mechanisms including the first examples of albicidin detoxification (TABLE 7). Strain SB1403, which showed the strongest albicidin detoxification, was characterized in more detail. Culture filtrates from this strain showed increasing extracellular activity as cultures aged from 24 h to 40 h. Culture filtrate from a 40 h culture abolished antibiotic activity of a 300 ng ml$^{-1}$ albicidin solution during a 6 h incubation, and no antibiotic activity was recovered upon boiling the mixture. The capacity of culture filtrate to inactivate albicidin was abolished by treatment with protease K. Cell extracts of strain SB1403 also caused progressive and irreversible inactivation of albicidin (FIG. 13). These observations indicate enzymatic detoxification of albicidin by strain SB1403.

Taxonomic identification. Strain SB1403 is a gram-negative, rod-shaped bacterium (0.6–1.0 $\mu$m×1.3–3.0 $\mu$m) with 4–8 peritrichous flagella. Colonies on SP agar are yellow. The strain was positive for oxidation and fermentation of glucose, production of β-galactosidase, metabolism of L-arabinose, cellobiose, glycerol, myo-inositol, maltose, N-acetyl-D-glucosamine, D-mannitol, D-mannose, L-rhamnose, sucrose and trehalose. The strain was negative in tests for phenylalanine deaminase, arginine dihydrolase, ornithine decarboxylase, metabolism of malonate, D-adonitol, lactose, lactulose, I-erythritol, L-fucose, turanose, xylitol, D-galacturonic acid lactone and N-acetyl-D-galactosamine. These characteristics allow identification of strain SB1403 as *Pantoea dispersa* (Gavini et al., 1989, International Journal of Systematic Bacteriology, 39, 337–345). However, strain SB1403 differed from previously characterized strains of *P. dispersa* by producing acid from raffinose, sorbitol and α-methyl-D-glucoside.

Biocontrol of leaf scald by *P. dispersa* SB1403. *P. dispersa* was very effective as a biocontrol against *X. albilineans* when applied to wounded sugarcane at the same time as the pathogen (Table 8). Sugarcane variety Q44 is highly susceptible to leaf scald disease, and develops severe symptoms in emerging leaves following inoculation with *X. albilineans*. The inoculum concentration used in this experiment resulted in death of 50% of inoculated leaves within 2 weeks, and an average of 14 characteristic white pencil lines power plant in surviving leaves. In plants co-inoculated with *P. dispersa* SB1403, no leaves died and there was a 98% reduction in the frequency of white pencil lines, even with a ten-fold excess of *X. albilineans* cells in the inoculum.

Biocontrol agent *P. dispersa* SB1403 invaded wounded sugarcane leaves without causing any visible symptoms or any apparent adverse effect on growth of the inoculated sugarcane plants. Six months after inoculation, it was present in young stem tissue of apparently healthy sugarcane plants at populations ca 10$^3$-fold higher than similar organisms in water-inoculated controls.

*X. albilineans* was readily reisolated from inoculated leaves showing white pencil lines. Six months after inoculation, over 90% of plants inoculated with *X. albilineans* alone were dead. In contrast, plants co-inoculated with the biocontrol agent developed no systemic leaf scald symptoms and the pathogen could not be reisolated, even on SP medium containing ampicillin, which permits growth of the pathogen but not the biocontrol agent.

Because *X. albilineans* is spread very efficiently during mechanical harvesting of sugarcane (Taylor et al., 1988, Sugar Cane, 1988 (4), 11–14), the high level of biocontrol provided by simultaneous application of *P. dispersa* SB1403 may be useful to restrict spread of the pathogen in the field. For example, the biocontrol agent could be applied by dripping onto base cutters or through spray nozzles directed at the freshly cut stubble. A similar approach could be used in mechanical cutter-planters, which are typically already equipped with a spray or dip system to apply fungicide to the cut ends of stalk sections before planting.

Strains of *Erwinia herbicola* (syn. Pantoea spp.; Gavini et al., 1989, International Journal of Systematic Bacteriology, 39, 337–345) providing biocontrol against fire blight caused by *Erwinia amylovora* (Vanneste et al., 1992, Journal of Bacteriology, 174, 2785–2796) or blackleg caused by *Leptosphaeria maculans* (Chakraborty et al., 1994, Letters in Applied Microbiology, 18, 74–76), produce antimicrobial substances antagonistic to those pathogens. P. dispersa SB1403 did not produce any detectable antibiotic effective against *E. coli* or *X. albilineans*. Rather, *P. dispersa* SB1403 produces a detoxification enzyme which protects this biocontrol agent against albicidin antibiotics produced by the pathogen. As albicidins are known to play a role in pathogenicity of *X. albilineans*, albicidin detoxification may act not only to favour colonisation by *P. dispersa* in competition with *X. albilineans* at wounds which are the primary sites of invasion, but also to protect the plant by removal of albicidin phytotoxins necessary as pathogenicity factors for establishment of the pathogen and development of systemic leaf scald disease in sugarcane.

EXAMPLE 3

Further Studies

Experiments demonstrating the effect of expression of albicidin detoxification enzyme in *X. albilineans*. A 806 bp SphI-pVUII fragment, containing the intact albD gene (including promoter, structure gene and terminator region) of *E. herbicola* SB1403 was blunt-ended and ligated into the HindII site of suicide vector pJP5603. The ligation product was used to transform *E. coli* JM109 ($\lambda$pir). A recombinant clone, pJPAIdSP was identified by restriction enzyme digestion and agrose gel electrophoresis. It was transferred into the mobilising strain S17-1 ($\lambda$pir), and mobilised into *X. albilineans* XA3 which is resistant to ampicillin. Exconjugant colonies were selected on the SP agar medium containing 50 $\mu$g/mL kanamycin and 200 $\mu$g/mL ampicillin, and tested for albicidin production and synthesis of AlbD enzyme. Genetically modified *X. albilineans* expressing albD failed to induce disease on susceptible sugarcane, while the parent *X. albilineans* strain induced severe symptoms. This further supports the importance of albicidin in pathogenicity and the use of the albD gene to confer disease resistance.

Experiments further demonstrating resistance of various sugarcane lines to leaf scald disease. The albD gene was modified for expression in plants, and introduced into leaf scald susceptible sugarcane cultivar Q63 by particle bombardment. More than 60 lines cobombarded with albD and the NPT-II gene have been regenerated, of which approximately half express the toxin resistance gene. Plants from 34 lines cobombarded with albD and 20 control lines were challenged with *X. albilineans*. Teb transgenic lines showed no disease symptoms under conditions which caused severe symptoms on controls (90% infection rate, average of 13 white pencil lines per plant on inoculated leaves and rapid death of many plants). This confirms the effectiveness of albD as a leaf scald disease resistance gene in transgenic sugarcane.

Experiments with the albicidin detoxification enzyme. The AlbD enzyme appears to be a hydrolyase. Two pieces of evidence support this suggestion. Firstly, purified AlbD enzyme combined with purified albicidin in water was found in inactivate albicidin. As no co-factors were required and other known mechanisms of activation cannot operate under these conditions, the mode of inactivation points to hydrolysis. Secondly, the inactivation reaction as analysed by HPLC showed the loss of albicidin with the production of two peaks representing the products of the reaction. Again, this result points towards an hydrolysis reaction.

TABLE 1

Bacterial strains and plasmids

| Strain or Plasmid* | Genotype or feature | Reference or source |
|---|---|---|
| *X. albilineans* XA3 | Sugarcane leaf scald pathogenic isolate, albicidin producer | This work |
| *E. herbicola* SB1403 | Alb$^r$ | This work |
| *E. herbicola* SB1403rif | Rifampincin resistant derivative of SB1403 Alb$^r$, Rif$^r$ | This work |
| *E. coli* DH5$\alpha$ | F$^-$deoR endA1 gryA96 hsdR17 (r$^-$ m$^+$) $\Delta$(lacZYA-argF)U169($\phi$80d lacZ$\Delta$M15) recA1 relA1 supE44 thi-1$\lambda^-$ Alb$^s$ | Sambrook et al. (1989) |
| PLASMID | | |
| pLAFR3 | Cosmid vector, Tc$^r$ | Murphy, P. |
| PBS SK+ | Cloning and Sequencing vector, Ap$^r$ | Stratagene |
| pKK223-3 | Bacterial expression vector, Ap$^r$ | Pharmacia |
| pGEM-2T | GST gene fusion vector, Ap$^r$ | Pharmacia |
| pJP5603 | Bacterial suicide vector, Kn$^r$ | Penfold and Pemberton |
| pSB6 | albB gene from *A. denitrificans* cloned in pBluescriptll SK+, Ap$^r$, Alb$^r$ | Basnayake and Birch, 1995 |
| pGEM-4Z | DNA cloning vector, Ap$^r$ | Promega |
| pBl101 | | Clontech |
| pEmuKN | nptll gene fused to pEmu Monocots promoter, Ap$^r$ | Last et al., 1991 |
| pAHC18 | luc gene fused to maize ubiquitin promoter, Ap$^r$ | Bruce et al., 1989 |

TABLE 1-continued

Bacterial strains and plasmids

| Strain or Plasmid* | Genotype or feature | Reference or source |
|---|---|---|
| pU3Z | Sugarcane expression vector containing ubi∫intron promoter region and nos 3' terminator sequence, Ap$^r$ | This work |
| pU3Zald | albD gene fused to ubi∫intron in vector pU3Z, Ap$^r$ | This work |
| pU3ZGUS | gus gene fused to ubi∫intron in vector pU3Z, Ap$^r$ | This work |
| pTacAld | albD gene fused to pTac promoter in vector pKK223-3, Ap$^r$, Alb$^r$ | This work |
| pGSTALD | albD gene fused to GST gene in vector pGEM-2T, Ap$^r$, Alb$^r$ | This work |
| pJPAldHS | An internal fragment of albD gene cloned in suicide vector pJP5603, Ap$^r$, Alb$^r$ | This work |

TABLE 2

Bacteria isolated from X. albilineans infected sugarcane plants

| SUGARCANE | | RESISTANCE TO ALBICIDIN (units/ml) | | |
|---|---|---|---|---|
| ISOLATE | ORIGIN | 50 | 500 | 1000 |
| SB101 | tip of inoculated leaf | + | + | + |
| SB107 | tip of inoculated leaf | + | + | + |
| SB109 | tip of inoculated leaf | + | − | − |
| SB501 | middle section of inoculated leaf | + | + | − |
| SB902 | middle of natural infected leaf | + | − | − |
| SB903 | middle of natural infected leaf | + | − | − |
| SB904 | middle of natural infected leaf | + | − | − |
| SB905 | middle of natural infected leaf | + | − | − |
| SB1301 | top part of cane | + | + | − |
| SB1401 | base part of cane | + | + | − |
| SB1402 | base part of cane | + | + | − |
| SB1403 | base part of cane | + | + | + |
| SB1404 | base part of cane | + | + | − |
| SB1405 | base part of cane | − | − | − |
| SB1406 | base part of cane | − | − | − |

TABLE 3

Albicidin resistant bacteria from sugarcane and their possible resistance mechanism

| | % ADDED ALBICIDIN ACTIVITY RECOVERED AFTER REACTION* | | PUTATIVE MECHANISM |
|---|---|---|---|
| TREATMENT | UNBOILED | BOILED | |
| Alb$^r$ (controls) | 100 | 90 | |
| +A. denitrificans | 59 | 68 | toxin binding |
| +DH5α(pSB6) | 0 | 55 | toxin binding |
| +RR1Alb$^r$ | 95 | 94 | toxin exclusion |
| +SB1401 | 0 | 23 | toxin binding |
| +SB1402 | 36 | 64 | |
| +SB501 | 91 | 73 | toxin or exclusion? |
| +SB1301 | 86 | 73 | or |
| +SB1404 | 91 | 75 | resistance target? |
| +SB101 | 45 | 41 | toxin inactivation |
| +SB107 | 46 | 41 | |
| +SB1403 | 9 | 0 | |

TABLE 4

Effect of E. herbicola SB1403 in biocontrol of leaf scald disease of sugarcane*

| Inoculum | Water | X.a$_{10}$ | X.a$_{10}$ E.h$_1$ | X.a$_{10}$ E.h$_{10}$ | X.a$_{10}$ E.h$_{100}$ | E.h$_{10}$ |
|---|---|---|---|---|---|---|
| Dead leaves | 0 | 20 | 0 | 0 | 0 | 0 |
| White pencil lines | 0 | 139 | 2 | 3 | 0 | 0 |

TABLE 5

Biocontrol effect of E. herbicola SB1403rif, SM1, SM18 on leaf scald disease of sugarcane caused by X. albilineans XA3

| TREATMENT | No. of white pencil lines | No. of dead leaves |
|---|---|---|
| Water | 0 | 0 |
| XA3(10) | 129 | 6 |
| XA3(10), SB1403rif(10$^{-1}$) | 1 | 0 |
| XA3(10), SB1403rif(10$^{-2}$) | 3 | 0 |
| XA3(10), SB1403rif(10$^{-3}$) | 5 | 0 |
| XA3(10), SM1(10$^{-1}$) | 8 | 0 |
| XA3(10), SM1(10$^{-2}$) | 9 | 0 |
| XA3(10), SM1(10$^{-3}$) | 26 | 0 |
| XA3(10), SM18(10$^{-1}$) | 9 | 0 |
| XA3(10), SM18(10$^{-1}$) | 11 | 0 |

TABLE 6

Correlation between albicidin detoxification and leaf scald resistance as indicated by absence of white pencil line symptoms in control and transgenic lines of sugarcane variety Q63

| Plant/Line | White pencil lines per plant | AlbD activity (zone reduction in mm diameter) |
|---|---|---|
| untransformed 1 | 6.3 | 0 |
| untransformed 1 | 8.1 | 0 |
| gus-1 | 5.8 | 0 |
| gus-2 | 6 | 0 |
| albD 804-3b | 0 | 8 |
| albD 804-3c | 0 | 7 |
| albD 804-3d | 0 | 9 |
| albD 811-4d | 0 | 7 |
| albD 811-4f | 0 | 9 |
| albD 811-4k | 6.7 | 0 |
| albD 811-5a | 0 | 8 |
| albD 811-5b | 0 | 9 |
| albD 811-5c | 8.3 | 0 |
| albD 811-6a | 0 | 9 |

TABLE 6-continued

Correlation between albicidin detoxification and leaf scald resistance as indicated by absence of white pencil line symptoms in control and transgenic lines of sugarcane variety Q63

| Plant/Line | White pencil lines per plant | AlbD activity (zone reduction in mm diameter) |
|---|---|---|
| albD 825-2a | 0 | 9 |
| albD 825-2c | 0 | 8 |

TABLE 7

Albicidin resistant bacteria from sugarcane, and possible resistance mechanisms

| Bacterial strain* | Level of albicidin resistance (ng/ml$^{-1}$) | Albicidin recovered after reaction (%) | | Probable Resistance Mechanism |
|---|---|---|---|---|
| | | Unboiled | Boiled | |
| E. coli RR1 | <50 | 78 | 87 | none |
| E. coli RR1 Alb$^r$ | >1000 | 95 | 94 | exclusion |
| E. coli DH5 pSB6 | >1000 | 0 | 55 | binding |
| A. denitrificans SO9 | >1000 | 59 | 68 | binding |
| SB501 | 500 | 91 | 73 | exclusion or resistant target |
| SB1301 | 500 | 86 | 73 | |
| SB1404 | 500 | 91 | 75 | |
| SB1401 | 500 | 0 | 23 | binding resistant target |
| SB1402 | 500 | 36 | 64 | |
| SB101 | >1000 | 45 | 41 | detoxification |
| SB107 | >1000 | 46 | 41 | |
| SB1403 | >1000 | 9 | 0 | |

TABLE 8

Biocontrol of sugarcane leaf scald disease by P. dispersa SB1403*

| INOCULUM† | | | |
|---|---|---|---|
| X. albilineans XA3 | P. dispersa SB1403 | DEAD LEAVES | WHITE PENCIL LINES |
| 0 | 0 | 0 | 6 |
| 10 | 0 | 20 | 139 |
| 10 | 1 | 0 | 2 |
| 10 | 10 | 0 | 3 |
| 10 | 100 | 0 | 0 |
| 0 | 10 | 0 | 0 |

LEGENDS

TABLE 1
* Plasmids constructed in albD gene cloning and sequencing are shown in FIG. 2.

TABLE 3
* The final concentration in the reaction mixture was 500 μ/mL, and each treatment has three replicates.

TABLE 4
* Each treatment has 10 plants. Symptoms were recorded from 4 newly emerged leaves after inoculation. X.a=X. albilineans XA3,E.h=E. herbicola SB1403. Numbers next to X.a and E.h represent relative proportion of bacterial cell numbers, with 10=4×10$^8$ C.F.U. (colony forming unit). The inoculation volumn for each plant was 200 μL.

TABLE 5
* Each treatment has 6 plants. Symptoms were recorded from 4 newly emerged leaves after inoculation. Numbers in bracket represent relative proportion of bacterial cell numbers used in inoculation, with 10=4×10$^8$ C.F.U. The inoculum volume for each plant was 200 μL.

TABLE 7
* Strains in the top panel are controls with known resistance mechanisms (Birch et al., 1990; Basnayake and Birch, 1995). Strains commencing with SB were isolated from diseased sugarcane in this study. Results are means of three replicates.

TABLE 8
* Symptoms were recorded 14 d after inoculation of sugarcane variety Q44, which is highly susceptible to leaf scald disease. Results are totals from four inoculated leaves on ten plants per treatment.
† Inoculum consisted of 200 μL volume containing the pathogen and biocontrol agent at the ratios shown, where 10 equals 4×10$^8$ colony forming units.

FIG. 1

Time course of albicidin detoxification by cell free extracts of E. herbicola SB1403. Denatured (boiling 5 min) and undenatured cell free extracts containing 100 μg total protein were added to TEMM buffer containing 300 ng of albicidin in a final volume of 100 μL, and incubated at 28° C. The reaction was stopped by boiling for 3 min. The reaction mixture was 10 centrifuged (14000 rpm) for 5 min before bioassay.

FIG. 2

Physical map of pQZB103 and its derivatives. The cloning vector pBluescriptII SK+ is represented by open boxes at both ends of the linearlized plasmid map. Except for pQZB103 and pQZH301, all other plasmids were generated by ExoIII unidirectional deletion. Albicidin resistance or sensitivity of each plasmid encoded in E. coli DH5α is indicated.

FIG. 3

Nucleotide sequence of the albD gene (SEQ ID NO:2) (FIGS. 3B–3F) and the predacated amino acid sequence (SEQ ID NO:1) (FIG. 3A) of its gene product. The PCR primers (SEQ ID NO:7 and SEQ ID NO:8) used for amplification of the coding region and elimination of a spurious (ATG) start codon are also shown.

FIG. 4

Best match of amino acids sequence of albD gene product (A) (SEQ ID NO:4) to the first 16 amino acids in the N-terminal of albicidin binding proteins encoded by A. denitrificans albB gene (B) (SEQ ID NO:5) and by K. oxytoca albA gene (C) (SEQ ID NO:6) Symbols: Double dot, identical amino acids; single dot, amino acids with similar properties in their side chains.

FIG. 5

Construction of suicide plasmid clone pJPAldHS for site-directed mutagenesis of albD gene in E. herbicola SB1403. (A) The internal HincII-StuI fragment (Shown as shadowed AldHS fragment, 326 bp) of albD gene was isolated and its relative distances to the ATG initiation and TAG stop codons were indicated. (B) Map of pJPAldHS. The AldHS fragment was ligated to the HincII site of suicide vector pJP5603, and the orientation of the AldHS fragment in pJPAldHS was determined by HincII and BamHI restriction enzymes double digestion.

FIG. 6

Inactivation of albicidin by E. coli DH5α [pQZE533] and E. coli DH5α [pSB6]. Plasmids pQZE533 and pSB6 contain albD gene cloned from E. herbicola SB1403 and albB gene from A. denitrificans, respectively.

FIG. 7

Construction of GST-albD gene fusion plasmid for purification of AlbD enzyme protein. (A) A 790 bp albD structural gene fragment was amplified by PCR using a pair of oligonucleotides primers from the plasmid clone pQZE533 which contains the intact albD gene from *E. herbicola* SB1403. The 5' primer (SEQ ID NO:7) covers the ATG initiation codon (underlined) region of albD gene, and contains a mismatch nucleoside C. (indicated by *) to replace the original nucleoside G. The 3' primer (SEQ ID NO:8) spans the region 38 bp downstream of the TAG termination codon. The BamHI and PvuII restriction enzyme sites on the oligonucleotides primers are indicated. (B) The PCR amplified albD structural gene fragment was digested by BamHI and PvuII and ligated to the GST gene fusion vector PGEX-2T linealized by BamHI and SmaI. The sequences (SEQ ID NO:10) in the fusion region are shown and the cleavage-recognition sequence of the site-specific protease Thrombin is indicated (SEQ ID NO:9). (C) Map of GST-albD gene fusion construct pGSTALD.

FIG. 8

Effect of temperature on AlbD enzyme activity. Purified AlbD enzyme and albicidin were mixed in 0.2M phosphate buffer, pH7.0 in final concentrations of 2 ng/$\mu$L AlbD enzyme and 15 u/$\mu$L albicidin; the reaction mixtures were incubated in water baths preset in different temperatures for 30 min. The reaction was stopped by boiling for 3 min. The albicidin remaining in the reaction mixture was assayed. Symbol: open bar, albicidin+AlbD; striped bar, albicidin only blank control. The albicidin used in this experiment was further purified using DE52 chromatography.

FIG. 9

Effect of pH on AlbD enzyme activity, the condition for the enzyme assay were described in FIG. 8 legend except the albicidin solutions were prepared in phosphate buffers of different pH. Symbol: solid bar, albicidin+AlbD; open bar albicidin only blank control.

FIG. 10

(A) The PCR amplified coding sequence of albD gene was fused to tac promoter for expressing of AlbD enzyme in *E. coli*. A pair of PCR primers flanking the start codon (underlined) (SEQ ID NO:7) and termination region (38 bp downstream the TAG stop codon) (SEQ ID NO:8) was used to amplify albD structural gene portion using plasmid clone pQZE533 as template. The 790 bp PCR product was digested by BamHI and PvuII, blunt ended by Klenow DNA polymerase before ligated to SmaI site of bacterial expression vector pKK223-3. (B) Map of resultant plasmid clone pTacAld showing right orientated albD structural gene portion is under the control of promoter Ptac.

FIG. 11

(A) Map of sugarcane expression vector pU3Z. Construction approaches have been described in Materials and Methods section. (B) The coding sequence of albD was amplified from plasmid clone pQZE533. The PCR product was digested with BamHI and PvuII and ligated to BamHI and SmaI linearlized vector pU3Z. (C) Map of resultant construct pU3ZaId.

FIG. 12

Frequency distribution of disease severity in sugarcane cultivar Q63 plant lines regenerated from callus co-bombarded with albD (2–10 replicate plants per line from 19 lines), and control lines not bombarded with albD (2–6 replicate plants per line from 9 lines). Experiment A, inoculated with *X. albilineans* XA3.

FIG. 13

Frequency distribution of disease severity in sugarcane cultivar Q63 plant lines regenerated from callus co-bombarded with albD (2–10 replicate plants per line from 34 lines), and control lines not bombarded with albD (2–6 replicate plants per line from 20 lines). Experiment B, inoculated with *X. albilineans* XA15.

I claim:

1. An isolated nucleotide sequence encoding an albicidin detoxification enzyme comprising the sequence of amino acids set forth in SEQ ID NO:1.

2. The isolated nucleotide sequence of claim 1 wherein the nucleotide sequence comprises the sequence of nucleotides set forth in SEQ ID NO:2.

3. The isolated nucleotide sequence of claim 1 wherein the nucleotide sequence comprises the sequence of nucleotides set forth in SEQ ID NO:3.

4. An isolated nucleotide sequence which hybridizes under stringent conditions with the sequence of nucleotides set forth in SEQ ID NO:2 or SEQ ID NO:3.

5. The isolated nucleotide sequence of claim 4 wherein said nucleotide sequence is obtained from a bacterium.

6. The isolated nucleotide sequence of claim 4 wherein said nucleotide sequence is obtained from a strain of Erwinia or Pantoea.

7. A method of producing a transgenic plant with enhanced resistance to albicidin and leaf scald disease, said method comprising the steps of introducing and expressing the nucleotide sequence of any one of claims 1 to 6 in a plant, plant part or plant cell, and growing the plant, plant part or plant cell to produce the transgenic plant.

8. A method of producing a transgenic plant with enhanced resistance to albicidin and leaf scald disease, said method comprising the steps of introducing and expressing the nucleotide sequence of any one of claims 1 to 6 in a plant, plant part or plant cell, and growing the plant, plant part or plant cell to produce the transgenic plant, wherein the step of introducing the nucleotide sequence is effected by particle bombardment.

9. A method of producing a transgenic plant with enhanced resistance to albicidin and leaf scald disease, said method comprising the steps of introducing and expressing the nucleotide sequence of any one of claims 1 to 6 in a plant, plant part or plant cell, and growing the plant, plant part or plant cell to produce the transgenic plant, wherein said plant, plant part or plant cell is or is obtained from a sugarcane variety.

10. A method of producing a transgenic plant with enhanced resistance to albicidin and leaf scald disease, said method comprising the steps of introducing into a plant, or plant part or cell thereof a vector comprising the nucleotide sequence of any one of claims 1 to 6 wherein said nucleotide sequence is operably linked to one or more regulatory nucleotide sequences, and growing said plant or plant part or cell thereof to produce said transgenic plant.

11. A method of producing a transgenic plant with enhanced resistance to albicidin and leaf scald disease, said method comprising the steps of introducing into a plant, or plant part or cell thereof a vector comprising the nucleotide sequence of any one of claims 1 to 6 wherein said nucleotide sequence is operably linked to one or more regulatory nucleotide sequences, and growing said plant or plant part or cell thereof to produce said transgenic plant, wherein the step of introducing the vector is effected by particle bombardment.

12. A method of producing a transgenic plant with enhanced resistance to albicidin and leaf scald disease, said method comprising the steps of introducing into a plant, or plot part or cell thereof a vector comprising the nucleotide sequence of any one of claims 1 to 6 wherein said nucleotide sequence is operably linked to one or more regulatory nucleotide sequences, and growing said plant or plant part or cell thereof to produce said transgenic plant, wherein said plant, plant part or plant cell is or is obtained from a sugarcane variety.

13. A transgenic plant with enhanced resistance to albicin and leaf scald disease, said plant comprising the nucleotide sequence of any one of claims 1 to 6 wherein said sequence is operably linked to one or more regulatory nucleotide sequences.

14. A transgenic sugarcane plant with enhanced resistance to albicidin and leaf scald disease, said plant comprising the nucleotide sequence of any one of claims 1 to 6 wherein said sequence is operably linked to one or more regulatory nucleotide sequences.

15. A transgenic plant with enhanced resistance to albicidin and leaf scald disease, said plant comprising the nucleotide sequence of any one of claims 1 to 6 wherein said sequence is operably linked to one or more regulatory nucleotide sequences and is stably incorporated within the genome of cells of said plant.

16. A transgenic sugarcane plant with enhanced resistance to albicidin and leaf scald disease, said plant comprising the nucleotide sequence of any one of claims 1 to 6 wherein said sequence is operably linked to one or more regulatory nucleotide sequences and is stably incorporated within the genome of cells of said plant.

17. A vector comprising the nucleotide sequence of any one of claims 1 to 6.

18. A vector comprising the nucleotide sequence of any one of claims 1 to 6 wherein said nucleotide sequence is operably linked to one or more regulatory nucleotide sequences.

* * * * *

SEQUENCE LISTING

```
<160> NUMBER OF SEQ ID NOS: 12

<210> SEQ ID NO 1
<211> LENGTH: 235
<212> TYPE: PRT
<213> ORGANISM: Erwinia herbicola

<400> SEQUENCE: 1

Met Asp Lys Ser Asp Leu Thr Glu Thr Ser Arg Ile Lys His Gly Glu
  1               5                  10                  15

Glu Ala Phe Asp Val Thr Leu Leu Gln Val Lys Gly Ala Thr Arg Cys
                 20                  25                  30

Ile Leu Phe Ala Ala Gly Leu Ser Gly Ser Pro Leu Arg His Leu Glu
             35                  40                  45

Leu Leu Gln Thr Phe Ala Arg His Gly Val Ser Val Ala Pro His
         50                  55                  60

Phe Glu Arg Leu Thr Ser Pro Val Pro Thr Arg Ala Glu Leu Leu Glu
 65                  70                  75                  80

Arg Cys Gln Arg Leu Ala Arg Ala Gln Asn Glu Phe Cys Ser Gly Tyr
                 85                  90                  95

Ala Ser Val Thr Gly Val Gly His Ser Leu Gly Ser Val Ile Leu Leu
                100                 105                 110

Leu Asn Ala Gly Ala Ile Ala Met Thr Ser Ala Gly Glu Ser Val Val
```

-continued

```
                115                 120                     125

Phe Ala Gly Asp Arg Met Leu His Arg Leu Ile Leu Leu Ala Pro Pro
            130                 135                 140

Ala Asp Phe Phe Gln Ala Pro Ser Ala Leu Ala Ala Val Asn Val Pro
        145                 150                 155                 160

Val His Ile Trp Ala Gly Glu Lys Asp Ser Leu Thr Pro Pro Ser Gln
                        165                 170                 175

Ala Cys Phe Leu Lys Gln Ala Leu Glu Gly Tyr Thr Gln Thr Tyr Leu
                    180                 185                 190

Cys Val Met Glu Glu Ala Gly His Phe Thr Phe Met Asn Thr Leu Pro
                195                 200                 205

Pro Gln Val Thr Asp Ser His Pro Ser Arg Glu Ala Phe Leu Leu Asp
            210                 215                 220

Leu Gly Glu Asn Ile Ala Arg Leu Val Thr Asp
        225                 230                 235
```

<210> SEQ ID NO 2
<211> LENGTH: 1016
<212> TYPE: DNA
<213> ORGANISM: Erwinia herbicola

<400> SEQUENCE: 2

```
atgcagaggg gctcaatgac gtttcatccc aatgtcctga ccagtcataa ttcaccaagc      60
cgaggtttgc tgtgtggcag aatggcatcc aacgcgtaaa ggtggcgaga gcctgttaat     120
attttttgaca atcggttaag cgggatgcgt tttgatggac aaaagtgatc tcacggaaac    180
gtctcggatc aaacatgggg aagaggcgtt tgacgtcacc ttattgcagg ttaagggggc     240
gacgcgctgt atccttttttg ctgcggggct gagcggcagt ccgctgcgcc atcttgaact    300
tctccagacc tttgcccgcc atggcgtttc cgttgtcgcg ccacactttg aacggttgac    360
ctcacccgtg cccaccagag ctgaattact ggaacgctgc cagcggcttg cgcgggctca    420
gaatgaattt tgtagcggtt atgcgtcggt taccggtgtt ggccactccc tgggtagcgt    480
gatttttattg ctgaatgccg ggctatagc gatgacaagc gcagggaat cggttgttttt    540
cgccggcgac cggatgttgc atcgacttat tttactggca ccgcccgccg attttttcca    600
ggctccgtct gcgctggcag cggtgaacgt acctgttcac atctgggcag gtgaaaagga    660
cagcctgacg cccccgtccc aggcctgctt tcttaaacag gcactggagg gttacacgca    720
gacttatctc tgtgtgatgg aagaggccgg gcatttttacc ttcatgaata ccttgcctcc    780
gcaggtaacc gattcacatc cgtcgcggga ggccttttctt ttagatttgg gcgaaaacat    840
agcccggctg gtgactgatt agcacagagg gcggggcgat gagattttttg cagggataac    900
ctcttccagc tgatacgatt caatcatact catcaaaagc atcatttcat cctgtcttag    960
gggctattgt gaaacagaaa tcggccctat agtgagtcgt attacgcccg ctcgaa       1016
```

<210> SEQ ID NO 3
<211> LENGTH: 704
<212> TYPE: DNA
<213> ORGANISM: Erwinia herbicola

<400> SEQUENCE: 3

```
atggacaaaa gtgatctcac ggaaacgtct cggatcaaac atggggaaga ggcgtttgac      60
gtcacctttat tgcaggttaa gggggcgacg cgctgtatcc ttttttgctgc ggggctgagc    120
ggcagtccgc tgcgccatct tgaacttctc cagaccttttg cccgccatgg cgtttccgtt    180
```

```
gtcgcgccac actttgaacg gttgacctca cccgtgccca ccagagctga attactggaa    240
cgctgccagc ggcttgcgcg ggctcagaat gaattttgta gcggttatgc gtcggttacc    300
ggtgttggcc actccctggg tagcgtgatt ttattgctga atgccggggc tatagcgatg    360
acaagcgcag gggaatcggt tgttttcgcc ggcgaccgga tgttgcatcg acttatttta    420
ctggcaccgc cgccgatttt tttccaggct ccgtctgcgc tggcagcggt gaacgtacct    480
gttcacatct gggcaggtga aaaggacagc ctgacgcccc cgtcccaggc ctgctttctt    540
aaacaggcac tggagggtta cacgcagact tatctctgtg tgatggaaga ggccgggcat    600
tttaccttca tgaataccTt gcctccgcag gtaaccgatt cacatccgtc gcgggaggcc    660
tttcttttag atttgggcga aaacatagcc cggctggtga ctga                    704
```

```
<210> SEQ ID NO 4
<211> LENGTH: 16
<212> TYPE: PRT
<213> ORGANISM: Erwinia herbicola

<400> SEQUENCE: 4

Leu Phe Ala Ala Gly Leu Ser Gly Ser Pro Leu Arg His Leu Glu Leu
  1               5                  10                  15

<210> SEQ ID NO 5
<211> LENGTH: 16
<212> TYPE: PRT
<213> ORGANISM: Alcaligenes dentrificans

<400> SEQUENCE: 5

Met Tyr Asp Lys Tyr Phe Ser Arg Glu Glu Leu Ala Arg Leu Pro Leu
  1               5                  10                  15

<210> SEQ ID NO 6
<211> LENGTH: 16
<212> TYPE: PRT
<213> ORGANISM: Klebsiella oxytoca

<400> SEQUENCE: 6

Met Tyr Asp Arg Trp Phe Ser Gln Gln Glu Leu Gln Val Leu Pro Phe
  1               5                  10                  15

<210> SEQ ID NO 7
<211> LENGTH: 25
<212> TYPE: DNA
<213> ORGANISM: Erwinia herbicola

<400> SEQUENCE: 7
ttaagcggga tccgttttga tggac                                          25

<210> SEQ ID NO 8
<211> LENGTH: 25
<212> TYPE: DNA
<213> ORGANISM: Erwinia herbicola

<400> SEQUENCE: 8
gattgaatcg tatcagctgg aagag                                          25

<210> SEQ ID NO 9
<211> LENGTH: 10
<212> TYPE: PRT
<213> ORGANISM: Erwinia herbicola

<400> SEQUENCE: 9
```

```
Leu Val Pro Arg Gly Ser Val Leu Met Asp
 1               5                  10
```

<210> SEQ ID NO 10
<211> LENGTH: 30
<212> TYPE: DNA
<213> ORGANISM: Erwinia herbicola

<400> SEQUENCE: 10
ctggttccgc gtggatccgt tttgatggac                              30

<210> SEQ ID NO 11
<211> LENGTH: 14
<212> TYPE: RNA
<213> ORGANISM: Erwinia herbicola

<400> SEQUENCE: 11
aucaccuccu uucu                                               14

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence:  Albicidin
      Binding Peptide Motif
<220> FEATURE:
<221> NAME/KEY: SIMILAR
<222> LOCATION: (1)..(16)
<223> OTHER INFORMATION: Best match Motif of SEQ ID NOS: 4-6 as
      explained regarding Fig. 4
<220> FEATURE:
<221> NAME/KEY: VARIANT
<222> LOCATION: (3)
<223> OTHER INFORMATION: Xaa can be Ala or Asp
<220> FEATURE:
<221> NAME/KEY: VARIANT
<222> LOCATION: (4)
<223> OTHER INFORMATION: Xaa can be Ala, Lys or Arg
<220> FEATURE:
<221> NAME/KEY: VARIANT
<222> LOCATION: (5)
<223> OTHER INFORMATION: Xaa can be Gly, Tyr or Trp
<220> FEATURE:
<221> NAME/KEY: VARIANT
<222> LOCATION: (8)
<223> OTHER INFORMATION: Xaa can be Gly, Arg or Gln
<220> FEATURE:
<221> NAME/KEY: VARIANT
<222> LOCATION: (9)
<223> OTHER INFORMATION: Xaa can be Ser, Glu or Gln
<220> FEATURE:
<221> NAME/KEY: VARIANT
<222> LOCATION: (10)
<223> OTHER INFORMATION: Xaa can be Pro or Glu
<220> FEATURE:
<221> NAME/KEY: VARIANT
<222> LOCATION: (12)
<223> OTHER INFORMATION: Xaa can be Arg, Ala or Gln
<220> FEATURE:
<221> NAME/KEY: VARIANT
<222> LOCATION: (13)
<223> OTHER INFORMATION: Xaa can be His, Arg or Val
<220> FEATURE:
<221> NAME/KEY: VARIANT
<222> LOCATION: (15)
<223> OTHER INFORMATION: Xaa can be Glu or Pro

<400> SEQUENCE: 12

```
Met Tyr Xaa Xaa Xaa Phe Ser Xaa Xaa Xaa Leu Xaa Xaa Leu Xaa Leu
 1               5                  10                  15
```